US012708085B2

(12) United States Patent
Anai et al.

(10) Patent No.: US 12,708,085 B2
(45) Date of Patent: Aug. 18, 2026

(54) SOYBEANS HAVING LOW FURAN FATTY ACID CONTENT

(71) Applicants: SAGA UNIVERSITY, Saga (JP); J-OIL MILLS, Inc., Tokyo (JP)

(72) Inventors: Toyoaki Anai, Fukuoka (JP); Satoshi Watanabe, Saga (JP); Naruto Makita, Tokyo (JP); Ryo Okabe, Tokyo (JP); Hisashi Arai, Tokyo (JP); Erina Hiyama, Tokyo (JP); Takashi Sano, Tokyo (JP)

(73) Assignees: SAGA UNIVERSITY, Saga (JP); J-OIL MILLS, Inc., Tokyo (JP)

( * ) Notice: Subject to any disclaimer, the term of this patent is extended or adjusted under 35 U.S.C. 154(b) by 253 days.

(21) Appl. No.: 18/272,831

(22) PCT Filed: Jan. 14, 2022

(86) PCT No.: PCT/JP2022/002307

§ 371 (c)(1),
(2) Date: Jul. 18, 2023

(87) PCT Pub. No.: WO2022/158583

PCT Pub. Date: Jul. 28, 2022

(65) Prior Publication Data

US 2024/0298599 A1 Sep. 12, 2024

(30) Foreign Application Priority Data

Jan. 21, 2021 (JP) ................................ 2021-007795

(51) Int. Cl.

| | |
|---|---|
| ***A01H 6/54*** | (2018.01) |
| ***A01H 1/02*** | (2006.01) |
| ***A23K 10/30*** | (2016.01) |
| ***A23L 33/115*** | (2016.01) |
| ***A61K 36/48*** | (2006.01) |
| ***C12N 15/82*** | (2006.01) |

(52) U.S. Cl.

CPC ............... *A01H 6/542* (2018.05); *A01H 1/02* (2013.01); *A23K 10/30* (2016.05); *A23L 33/115* (2016.08); *A61K 36/48* (2013.01); *C12N 15/8247* (2013.01)

(58) Field of Classification Search

None

See application file for complete search history.

(56) References Cited

U.S. PATENT DOCUMENTS

| | | | |
|---|---|---|---|
| 2010/0074999 | A1 | 3/2010 | Kamegai et al. |
| 2015/0322447 | A1 | 11/2015 | Denolf et al. |

FOREIGN PATENT DOCUMENTS

| | | | |
|---|---|---|---|
| JP | 4290222 | B | 7/2009 |
| WO | WO2010/150901 | A | 12/2010 |
| WO | WO 2017/033674 | A1 | 3/2017 |

OTHER PUBLICATIONS

Kao, J. et al., 1998; JAOCS vol. 75, No. 7: pp. 831-835. (Year: 1998).*

Wu, X. et al., JAOCS (1997) vol. 74, No. 9; pp. 1099-1103. (Year: 1997).*

Anai Toyoaki, Development of soybean mutant resources and identification of novel mutant alleles. Breeding Research, Nov. 11, 2020, vol. 22.

Sano, T., Effect of Furan Fatty Acids and 3-Methyl-2,4-nonanedione on Light-Induced Off-Odor in Soybean Oil, Journal of Agriculturaland Food Chemistry, Feb. 18, 2017, vol. 65, pp. 2136-2140.

Kitamura Keisuke, Characteristics and utilization of lipoxygenase deficiency soybean, Food Science, 1996, vol. 38, No. 8, pp. 102-107.

Office Action dated Oct. 7, 2025; Japanese patent application No. 2022-576766.

* cited by examiner

*Primary Examiner* — Russell Kallis

(74) *Attorney, Agent, or Firm* — RANKIN, HILL & CLARK LLP; Erik J. Overberger

(57) ABSTRACT

Provided are: modified soybeans having a reduced furan fatty acid content in the oils and fats contained in the soybeans; and uses of the modified soybeans. The present invention relates to modified soybeans in which the content ratio of furan fatty acid in the oils and fats contained in the soybeans has been reduced by genetic mutation.

18 Claims, 12 Drawing Sheets

Specification includes a Sequence Listing.

SEQUENCE LISTING

```
<160> NUMBER OF SEQ ID NOS: 13

<210> SEQ ID NO 1
<211> LENGTH: 3216
<212> TYPE: DNA
<213> ORGANISM: Glycine max
<220> FEATURE:
<221> NAME/KEY: CDS
<222> LOCATION: (291)..(2876)
```

```
<400> SEQUENCE: 1

gataacggct gttggaaaac aacccttac gtttaacgtg aataggaatc aatcactatt      60

attaatttag tactttcaac ttgcaactcc cttgtatgtg gacctttgag ttccacgtat    120

gtatacaatc catccatttg atacttgagt gctaccctca ttcttattaa agggtctttt    180

tgggttgttc tatgtatgca cattttcaga ttgcggcact tgaattaagg gaaaagggtt    240

gaaacttact ggtttttgtt acatagtaaa ctaaatagta gagagcaagg atg aga      296
                                                        Met Arg
                                                        1

gtt gca gtg gtt ggt agt ggg att agt ggg ttg gct tca gct tat ctt      344
Val Ala Val Val Gly Ser Gly Ile Ser Gly Leu Ala Ser Ala Tyr Leu
        5                   10                  15

ttg gcc aaa ggg gga gtg aat gtg gtg ctc tat gag aag gag gat tcg      392
Leu Ala Lys Gly Gly Val Asn Val Val Leu Tyr Glu Lys Glu Asp Ser
    20                  25                  30

ttg gga gga cat gcc aag act gtg aat gtt gat ggg gtt gat gtt gac      440
Leu Gly Gly His Ala Lys Thr Val Asn Val Asp Gly Val Asp Val Asp
35                  40                  45                  50

ctt ggc ttc atg gtc ttc aat cgg gtc acc tat cct aac atg ttg gat      488
Leu Gly Phe Met Val Phe Asn Arg Val Thr Tyr Pro Asn Met Leu Asp
                55                  60                  65

ttt ttt gag aat ctt gga gtt gac atg gaa tca tca gac atg tct ttt      536
Phe Phe Glu Asn Leu Gly Val Asp Met Glu Ser Ser Asp Met Ser Phe
            70                  75                  80

tct gtt agt tta gac aaa ggt cgt gga tgc gaa tgg gga agc aga aat      584
Ser Val Ser Leu Asp Lys Gly Arg Gly Cys Glu Trp Gly Ser Arg Asn
        85                  90                  95

ggt ttg tca agc ttg ttt gca cag aag aag aat gta ctg aat cct tac      632
Gly Leu Ser Ser Leu Phe Ala Gln Lys Lys Asn Val Leu Asn Pro Tyr
    100                 105                 110

ttc tgg caa atg ata agg gaa att gtc aag ttc aaa gat gat gtt att      680
Phe Trp Gln Met Ile Arg Glu Ile Val Lys Phe Lys Asp Asp Val Ile
115                 120                 125                 130

agc tat ctt gat atg ctt gag aat aac cca gat att gac cgc aac gag      728
Ser Tyr Leu Asp Met Leu Glu Asn Asn Pro Asp Ile Asp Arg Asn Glu
                135                 140                 145

cct cta ggg gaa ttc atc aag tca agg ggt tac tcc gaa tta ttt cag      776
Pro Leu Gly Glu Phe Ile Lys Ser Arg Gly Tyr Ser Glu Leu Phe Gln
            150                 155                 160

aaa gcc tat ctt att cca att tgt ggt tct atc tgg tcc tgc tct tct      824
Lys Ala Tyr Leu Ile Pro Ile Cys Gly Ser Ile Trp Ser Cys Ser Ser
        165                 170                 175

gaa gga gtt atg agt ttc tct gct ttc tca gtt ctt tca ttc tgt cgc      872
Glu Gly Val Met Ser Phe Ser Ala Phe Ser Val Leu Ser Phe Cys Arg
    180                 185                 190

aac cac cat cta ctt cag ctc ttt ggc aga cca cag tgg cta act gta      920
Asn His His Leu Leu Gln Leu Phe Gly Arg Pro Gln Trp Leu Thr Val
195                 200                 205                 210

aga tgg cgc tca caa act tat gtt aat aag gtc aaa caa gag ctt gag      968
Arg Trp Arg Ser Gln Thr Tyr Val Asn Lys Val Lys Gln Glu Leu Glu
                215                 220                 225

agg gaa ggt agt caa ata ata act aat cgt gag gtt cac ttg gtt tcg     1016
Arg Glu Gly Ser Gln Ile Ile Thr Asn Arg Glu Val His Leu Val Ser
            230                 235                 240

acg aca tct gaa aaa gga tgt gtt gtg tac tgc aat gat ggt tct caa     1064
Thr Thr Ser Glu Lys Gly Cys Val Val Tyr Cys Asn Asp Gly Ser Gln
        245                 250                 255

gaa atg tat gat gga tgc ata atg gca gtg cat gca cct gat gcc ttg     1112
```

-continued

```
Glu Met Tyr Asp Gly Cys Ile Met Ala Val His Ala Pro Asp Ala Leu
    260                 265                 270

cga tta tta gga gat gaa gca aca tat gat gag cga aga ata ctc gga      1160
Arg Leu Leu Gly Asp Glu Ala Thr Tyr Asp Glu Arg Arg Ile Leu Gly
275                 280                 285                 290

gct ttt caa tat gct tac agt gat att ttt ctt cat cgt gac aaa aat      1208
Ala Phe Gln Tyr Ala Tyr Ser Asp Ile Phe Leu His Arg Asp Lys Asn
                295                 300                 305

tta atg ccc caa aac cca gca gca tgg agt gca tgg aat ttt ctt ggt      1256
Leu Met Pro Gln Asn Pro Ala Ala Trp Ser Ala Trp Asn Phe Leu Gly
            310                 315                 320

agt aac aac aac aaa gtt tgt cta aca tac tgg atc aat att ctt cag      1304
Ser Asn Asn Asn Lys Val Cys Leu Thr Tyr Trp Ile Asn Ile Leu Gln
        325                 330                 335

aat att aaa gag aca agt caa ccc ttt ctt gta act ctc aat cca gac      1352
Asn Ile Lys Glu Thr Ser Gln Pro Phe Leu Val Thr Leu Asn Pro Asp
    340                 345                 350

cat ata cca gaa aat acc ttg cta aag tgg tca act ggc cat cca gtc      1400
His Ile Pro Glu Asn Thr Leu Leu Lys Trp Ser Thr Gly His Pro Val
355                 360                 365                 370

cca tca gtt gct gca ttc aaa gct tca tta gag ctt gac cat att caa      1448
Pro Ser Val Ala Ala Phe Lys Ala Ser Leu Glu Leu Asp His Ile Gln
                375                 380                 385

ggg aaa aga aaa atc tgg ttt tca gga gca tac caa ggt tat gga ttt      1496
Gly Lys Arg Lys Ile Trp Phe Ser Gly Ala Tyr Gln Gly Tyr Gly Phe
            390                 395                 400

cat gaa gat gga ttt aag gct ggc atg atc gca gct cat ggc att cta      1544
His Glu Asp Gly Phe Lys Ala Gly Met Ile Ala Ala His Gly Ile Leu
        405                 410                 415

gga agc tgc tgt gcc ctt cag acc aac cca aaa cac atg gta cct tct      1592
Gly Ser Cys Cys Ala Leu Gln Thr Asn Pro Lys His Met Val Pro Ser
    420                 425                 430

tgg aag gaa ctg gga gca cgc att ttt gtg act aga ttc ctg agt tgc      1640
Trp Lys Glu Leu Gly Ala Arg Ile Phe Val Thr Arg Phe Leu Ser Cys
435                 440                 445                 450

tat atc act act ggt tgt tta atg tta ctg gaa gag gga gga aca atg      1688
Tyr Ile Thr Thr Gly Cys Leu Met Leu Leu Glu Glu Gly Gly Thr Met
                455                 460                 465

ttc acc ttt gag gga act ggg aaa aac tgt ggt ctg aag agt gtt ttg      1736
Phe Thr Phe Glu Gly Thr Gly Lys Asn Cys Gly Leu Lys Ser Val Leu
            470                 475                 480

agg gtc cac gat cca caa ttt tat tgg aag gtg atg aca cag gca gat      1784
Arg Val His Asp Pro Gln Phe Tyr Trp Lys Val Met Thr Gln Ala Asp
        485                 490                 495

tta ggc ctt gca gat gca tat atc aat ggg gac ttt tca ttt gtt gat      1832
Leu Gly Leu Ala Asp Ala Tyr Ile Asn Gly Asp Phe Ser Phe Val Asp
    500                 505                 510

aaa gat gaa ggt ctc ttg aat ctt att ttg att ctc ata gcc aac aga      1880
Lys Asp Glu Gly Leu Leu Asn Leu Ile Leu Ile Leu Ile Ala Asn Arg
515                 520                 525                 530

gat tca aat gca tcc aac tca aaa ctg aag aag aat agg ggt tgg tgg      1928
Asp Ser Asn Ala Ser Asn Ser Lys Leu Lys Lys Asn Arg Gly Trp Trp
                535                 540                 545

aca ccc gtt ttc ttt acg tct gct ttg aca tct gca aag ttc ttc atg      1976
Thr Pro Val Phe Phe Thr Ser Ala Leu Thr Ser Ala Lys Phe Phe Met
            550                 555                 560

gat cat gtt tca agg cga aat act ctc acg cag gct cgc agg aac atc      2024
Asp His Val Ser Arg Arg Asn Thr Leu Thr Gln Ala Arg Arg Asn Ile
        565                 570                 575
```

-continued

```
tct agg cat tat gat ctg agc aat gac ctc ttt gcg act ttc ttg gat     2072
Ser Arg His Tyr Asp Leu Ser Asn Asp Leu Phe Ala Thr Phe Leu Asp
    580                 585                 590

gaa aca atg aca tat tca tgt gca gtg ttc aag aat aaa gat gaa gac     2120
Glu Thr Met Thr Tyr Ser Cys Ala Val Phe Lys Asn Lys Asp Glu Asp
595                 600                 605                 610

ttg aaa gat gca caa aag aga aaa atc tct ctc ctg att gaa aaa gct     2168
Leu Lys Asp Ala Gln Lys Arg Lys Ile Ser Leu Leu Ile Glu Lys Ala
                615                 620                 625

aga ata gat aag aca cat gaa att ctt gag att gga tgt gga tgg gga     2216
Arg Ile Asp Lys Thr His Glu Ile Leu Glu Ile Gly Cys Gly Trp Gly
            630                 635                 640

agt tta gcc att gaa gtt gtc aaa caa acc ggc tgc aaa tac act ggt     2264
Ser Leu Ala Ile Glu Val Val Lys Gln Thr Gly Cys Lys Tyr Thr Gly
        645                 650                 655

atc act ttg tct gag gag caa ctg aaa ctt gca gaa caa aga gtt aaa     2312
Ile Thr Leu Ser Glu Glu Gln Leu Lys Leu Ala Glu Gln Arg Val Lys
    660                 665                 670

gat gct ggg ctt cag gac cgc atc aat ttt gtt cta tgc gac tat cgc     2360
Asp Ala Gly Leu Gln Asp Arg Ile Asn Phe Val Leu Cys Asp Tyr Arg
675                 680                 685                 690

caa ttg ccc aag aca tat aaa tac gat agg att ata tct tgt gaa atg     2408
Gln Leu Pro Lys Thr Tyr Lys Tyr Asp Arg Ile Ile Ser Cys Glu Met
                695                 700                 705

ata gaa gct gtt ggt cat gaa tac atg gaa gag ttc ttt ggc tgt tgt     2456
Ile Glu Ala Val Gly His Glu Tyr Met Glu Glu Phe Phe Gly Cys Cys
            710                 715                 720

gaa tca gta ttg gcg gat aat gga ctt ctt gtt ctc cag ttc ata tca     2504
Glu Ser Val Leu Ala Asp Asn Gly Leu Leu Val Leu Gln Phe Ile Ser
        725                 730                 735

atc ccg gat gag cgt tat gat gaa tat agg cgc agt tct gat ttt ata     2552
Ile Pro Asp Glu Arg Tyr Asp Glu Tyr Arg Arg Ser Ser Asp Phe Ile
    740                 745                 750

aag gaa tat ata ttt cca gga ggt tgc cta ccc tct cta agt agg ata     2600
Lys Glu Tyr Ile Phe Pro Gly Gly Cys Leu Pro Ser Leu Ser Arg Ile
755                 760                 765                 770

aca tct gcc atg gca gcc aca tcc aga cta tgc gtg gag cac gtt gaa     2648
Thr Ser Ala Met Ala Ala Thr Ser Arg Leu Cys Val Glu His Val Glu
                775                 780                 785

aac ata ggt att cat tac tac caa aca ctc aga tgc tgg aga aaa aac     2696
Asn Ile Gly Ile His Tyr Tyr Gln Thr Leu Arg Cys Trp Arg Lys Asn
            790                 795                 800

ttc ttg aaa agg cag aat gaa att ttg gct ctc gga ttc aat gaa aaa     2744
Phe Leu Lys Arg Gln Asn Glu Ile Leu Ala Leu Gly Phe Asn Glu Lys
        805                 810                 815

ttt atc agg aca tgg gaa tac tat ttt gat tac tgt ggt gca ggt ttt     2792
Phe Ile Arg Thr Trp Glu Tyr Tyr Phe Asp Tyr Cys Gly Ala Gly Phe
    820                 825                 830

aag tca ctc aca cta ggg aat tat cag gtg gtt ttc tca cgc cct ggt     2840
Lys Ser Leu Thr Leu Gly Asn Tyr Gln Val Val Phe Ser Arg Pro Gly
835                 840                 845                 850

aac gtt cct gca tta ggc gat cca tac aaa agc tag accaaaacca          2886
Asn Val Pro Ala Leu Gly Asp Pro Tyr Lys Ser
                855                 860

gttgacagaa caagcctcac acattctacc aaagtgcatt acatgatggt gccaccatgt   2946

atctcctttc ttgataatct cgaagtaatt tttttgtcaa tatagatctc ttgtacattg   3006

ttaaaataga ggagctgaaa tgtgctgttt tgccgtggca aacagcaaga ttggtgagaa   3066

gtttttctca caaatgatat ttttttaaaa aggaacaagc ttattgatgc ccaaaaacaa   3126
```

ataactcatt aaatttctgt gtaacttttt atcccgtagc tgacaagtaa acatataata 3186 ttatccctat tttgctaatt ttcattatct 3216

<210> SEQ ID NO 2
<211> LENGTH: 861
<212> TYPE: PRT
<213> ORGANISM: Glycine max

<400> SEQUENCE: 2

Met Arg Val Ala Val Val Gly Ser Gly Ile Ser Gly Leu Ala Ser Ala
1 5 10 15

Tyr Leu Leu Ala Lys Gly Gly Val Asn Val Val Leu Tyr Glu Lys Glu
20 25 30

Asp Ser Leu Gly Gly His Ala Lys Thr Val Asn Val Asp Gly Val Asp
35 40 45

Val Asp Leu Gly Phe Met Val Phe Asn Arg Val Thr Tyr Pro Asn Met
50 55 60

Leu Asp Phe Phe Glu Asn Leu Gly Val Asp Met Glu Ser Ser Asp Met
65 70 75 80

Ser Phe Ser Val Ser Leu Asp Lys Gly Arg Gly Cys Glu Trp Gly Ser
85 90 95

Arg Asn Gly Leu Ser Ser Leu Phe Ala Gln Lys Lys Asn Val Leu Asn
100 105 110

Pro Tyr Phe Trp Gln Met Ile Arg Glu Ile Val Lys Phe Lys Asp Asp
115 120 125

Val Ile Ser Tyr Leu Asp Met Leu Glu Asn Asn Pro Asp Ile Asp Arg
130 135 140

Asn Glu Pro Leu Gly Glu Phe Ile Lys Ser Arg Gly Tyr Ser Glu Leu
145 150 155 160

Phe Gln Lys Ala Tyr Leu Ile Pro Ile Cys Gly Ser Ile Trp Ser Cys
165 170 175

Ser Ser Glu Gly Val Met Ser Phe Ser Ala Phe Ser Val Leu Ser Phe
180 185 190

Cys Arg Asn His His Leu Leu Gln Leu Phe Gly Arg Pro Gln Trp Leu
195 200 205

Thr Val Arg Trp Arg Ser Gln Thr Tyr Val Asn Lys Val Lys Gln Glu
210 215 220

Leu Glu Arg Glu Gly Ser Gln Ile Ile Thr Asn Arg Glu Val His Leu
225 230 235 240

Val Ser Thr Thr Ser Glu Lys Gly Cys Val Val Tyr Cys Asn Asp Gly
245 250 255

Ser Gln Glu Met Tyr Asp Gly Cys Ile Met Ala Val His Ala Pro Asp
260 265 270

Ala Leu Arg Leu Leu Gly Asp Glu Ala Thr Tyr Asp Glu Arg Arg Ile
275 280 285

Leu Gly Ala Phe Gln Tyr Ala Tyr Ser Asp Ile Phe Leu His Arg Asp
290 295 300

Lys Asn Leu Met Pro Gln Asn Pro Ala Ala Trp Ser Ala Trp Asn Phe
305 310 315 320

Leu Gly Ser Asn Asn Asn Lys Val Cys Leu Thr Tyr Trp Ile Asn Ile
325 330 335

Leu Gln Asn Ile Lys Glu Thr Ser Gln Pro Phe Leu Val Thr Leu Asn
340 345 350

-continued

```
Pro Asp His Ile Pro Glu Asn Thr Leu Leu Lys Trp Ser Thr Gly His
        355                 360                 365

Pro Val Pro Ser Val Ala Ala Phe Lys Ala Ser Leu Glu Leu Asp His
    370                 375                 380

Ile Gln Gly Lys Arg Lys Ile Trp Phe Ser Gly Ala Tyr Gln Gly Tyr
385                 390                 395                 400

Gly Phe His Glu Asp Gly Phe Lys Ala Gly Met Ile Ala Ala His Gly
                405                 410                 415

Ile Leu Gly Ser Cys Cys Ala Leu Gln Thr Asn Pro Lys His Met Val
            420                 425                 430

Pro Ser Trp Lys Glu Leu Gly Ala Arg Ile Phe Val Thr Arg Phe Leu
        435                 440                 445

Ser Cys Tyr Ile Thr Thr Gly Cys Leu Met Leu Leu Glu Glu Gly Gly
    450                 455                 460

Thr Met Phe Thr Phe Glu Gly Thr Gly Lys Asn Cys Gly Leu Lys Ser
465                 470                 475                 480

Val Leu Arg Val His Asp Pro Gln Phe Tyr Trp Lys Val Met Thr Gln
                485                 490                 495

Ala Asp Leu Gly Leu Ala Asp Ala Tyr Ile Asn Gly Asp Phe Ser Phe
            500                 505                 510

Val Asp Lys Asp Glu Gly Leu Leu Asn Leu Ile Leu Ile Leu Ile Ala
        515                 520                 525

Asn Arg Asp Ser Asn Ala Ser Asn Ser Lys Leu Lys Lys Asn Arg Gly
    530                 535                 540

Trp Trp Thr Pro Val Phe Phe Thr Ser Ala Leu Thr Ser Ala Lys Phe
545                 550                 555                 560

Phe Met Asp His Val Ser Arg Arg Asn Thr Leu Thr Gln Ala Arg Arg
                565                 570                 575

Asn Ile Ser Arg His Tyr Asp Leu Ser Asn Asp Leu Phe Ala Thr Phe
            580                 585                 590

Leu Asp Glu Thr Met Thr Tyr Ser Cys Ala Val Phe Lys Asn Lys Asp
        595                 600                 605

Glu Asp Leu Lys Asp Ala Gln Lys Arg Lys Ile Ser Leu Leu Ile Glu
    610                 615                 620

Lys Ala Arg Ile Asp Lys Thr His Glu Ile Leu Glu Ile Gly Cys Gly
625                 630                 635                 640

Trp Gly Ser Leu Ala Ile Glu Val Val Lys Gln Thr Gly Cys Lys Tyr
                645                 650                 655

Thr Gly Ile Thr Leu Ser Glu Glu Gln Leu Lys Leu Ala Glu Gln Arg
            660                 665                 670

Val Lys Asp Ala Gly Leu Gln Asp Arg Ile Asn Phe Val Leu Cys Asp
        675                 680                 685

Tyr Arg Gln Leu Pro Lys Thr Tyr Lys Tyr Asp Arg Ile Ile Ser Cys
    690                 695                 700

Glu Met Ile Glu Ala Val Gly His Glu Tyr Met Glu Glu Phe Phe Gly
705                 710                 715                 720

Cys Cys Glu Ser Val Leu Ala Asp Asn Gly Leu Leu Val Leu Gln Phe
                725                 730                 735

Ile Ser Ile Pro Asp Glu Arg Tyr Asp Glu Tyr Arg Arg Ser Ser Asp
            740                 745                 750

Phe Ile Lys Glu Tyr Ile Phe Pro Gly Gly Cys Leu Pro Ser Leu Ser
        755                 760                 765

Arg Ile Thr Ser Ala Met Ala Ala Thr Ser Arg Leu Cys Val Glu His
```

```
    770                 775                 780

Val Glu Asn Ile Gly Ile His Tyr Tyr Gln Thr Leu Arg Cys Trp Arg
785                 790                 795                 800

Lys Asn Phe Leu Lys Arg Gln Asn Glu Ile Leu Ala Leu Gly Phe Asn
                805                 810                 815

Glu Lys Phe Ile Arg Thr Trp Glu Tyr Tyr Phe Asp Tyr Cys Gly Ala
            820                 825                 830

Gly Phe Lys Ser Leu Thr Leu Gly Asn Tyr Gln Val Val Phe Ser Arg
        835                 840                 845

Pro Gly Asn Val Pro Ala Leu Gly Asp Pro Tyr Lys Ser
    850                 855                 860


<210> SEQ ID NO 3
<211> LENGTH: 1787
<212> TYPE: DNA
<213> ORGANISM: Glycine max
<220> FEATURE:
<221> NAME/KEY: CDS
<222> LOCATION: (312)..(1448)

<400> SEQUENCE: 3

aaaagagcat ctgcaaaaga taaggagaca ctcactgcca ttcctactct tacaaacctt      60

cttcagaact tcaactcttc gatctcctcc actttgcgca tcgtactctc tctctttctc     120

tctctctctc ttaccttctc aactcaacat caaaacaata tcaattctaa taataactca     180

ttgcacacgt caaatgaata gaagaagata attttgcaat atcacgtgat tttgaagatg     240

aatatcgatc gatatcgtgt ccggtactac tatttcagct ttacaggaaa tgcccatagc     300

aatcaacact g atg agc caa aat ctc aac atc gtg aat tac cga ttg ctt      350
             Met Ser Gln Asn Leu Asn Ile Val Asn Tyr Arg Leu Leu
             1               5                   10

tct tca agc ttg tgc ttg gaa aca atc tca aat aca ggg aca atg cag      398
Ser Ser Ser Leu Cys Leu Glu Thr Ile Ser Asn Thr Gly Thr Met Gln
    15                  20                  25

ctt gca tac gag act gtt gtg aag ctc atg ctg gct gca ctc gaa cgc      446
Leu Ala Tyr Glu Thr Val Val Lys Leu Met Leu Ala Ala Leu Glu Arg
30                  35                  40                  45

aac gtg ctc cct gac gtc atc acc agg aga ctc acg cgc ttg ctg ttg      494
Asn Val Leu Pro Asp Val Ile Thr Arg Arg Leu Thr Arg Leu Leu Leu
                50                  55                  60

gct act cgc ctt cgc tct gct tac aaa ccc tcc tcc caa ctt caa ctc      542
Ala Thr Arg Leu Arg Ser Ala Tyr Lys Pro Ser Ser Gln Leu Gln Leu
            65                  70                  75

tcc gat ctc ctc tac ttc gcg cat tca tta caa gag atg ccc ata gca      590
Ser Asp Leu Leu Tyr Phe Ala His Ser Leu Gln Glu Met Pro Ile Ala
        80                  85                  90

atc aac act gac aag cct aag tct caa cat tat gaa tta cca acc gct      638
Ile Asn Thr Asp Lys Pro Lys Ser Gln His Tyr Glu Leu Pro Thr Ala
    95                  100                 105

ttc ttc aag ctc gtc ctc gga aac aat ctc aaa tac agc tgt tgt tat      686
Phe Phe Lys Leu Val Leu Gly Asn Asn Leu Lys Tyr Ser Cys Cys Tyr
110                 115                 120                 125

ttc tct tct gcc tca atg acg ctg gat gat gct gaa gaa gca atg ttg      734
Phe Ser Ser Ala Ser Met Thr Leu Asp Asp Ala Glu Glu Ala Met Leu
                130                 135                 140

aaa ctg tac tgt gag aga tca aac ctg aaa gat ggt cat aca gtg ctt      782
Lys Leu Tyr Cys Glu Arg Ser Asn Leu Lys Asp Gly His Thr Val Leu
            145                 150                 155

gat gtg gga tgc ggt tgg gga tcg ttg gct cta tac att gcc aag aat      830
```

-continued

```
Asp Val Gly Cys Gly Trp Gly Ser Leu Ala Leu Tyr Ile Ala Lys Asn
        160                 165                 170

tac act aac tgt agg gtt aca gga atc tgc aat tcc aca act caa aag      878
Tyr Thr Asn Cys Arg Val Thr Gly Ile Cys Asn Ser Thr Thr Gln Lys
    175                 180                 185

gct tat att gag gag aag tgt agg gat ctt cag ctg caa aat ttg aat      926
Ala Tyr Ile Glu Glu Lys Cys Arg Asp Leu Gln Leu Gln Asn Leu Asn
190                 195                 200                 205

att ata gtt gct gat att agc aca ttt gaa atg gag act tct tat gac      974
Ile Ile Val Ala Asp Ile Ser Thr Phe Glu Met Glu Thr Ser Tyr Asp
                210                 215                 220

aga ata ttt tcc ata gaa atg ttt gag cat atg aag aac tat aaa gat     1022
Arg Ile Phe Ser Ile Glu Met Phe Glu His Met Lys Asn Tyr Lys Asp
            225                 230                 235

ctt ctg aag aag ata tcc aaa tgg atg aaa gag gat agc ctt tta ttt     1070
Leu Leu Lys Lys Ile Ser Lys Trp Met Lys Glu Asp Ser Leu Leu Phe
        240                 245                 250

gtt cat tac ttc tgc cac aaa gca ttt gcc tac cac ttt gag gac aaa     1118
Val His Tyr Phe Cys His Lys Ala Phe Ala Tyr His Phe Glu Asp Lys
    255                 260                 265

aat gaa gat gac tgg att aca aga tac ttc ttt act gga gga act atg     1166
Asn Glu Asp Asp Trp Ile Thr Arg Tyr Phe Phe Thr Gly Gly Thr Met
270                 275                 280                 285

cct tcg gca aat cta ctt ctt tat ttc caa gat gat gtt act gtc acc     1214
Pro Ser Ala Asn Leu Leu Leu Tyr Phe Gln Asp Asp Val Thr Val Thr
                290                 295                 300

aac cat tgg cta gta aat ggg aaa cac tac gca cag acc agt gaa gaa     1262
Asn His Trp Leu Val Asn Gly Lys His Tyr Ala Gln Thr Ser Glu Glu
            305                 310                 315

tgg ctc aaa aga atg gac cag aga atg act ttc atc aag cca att atg     1310
Trp Leu Lys Arg Met Asp Gln Arg Met Thr Phe Ile Lys Pro Ile Met
        320                 325                 330

caa tca aca tac ggc aag gac tca gct acc aag tgg act gct tat tgg     1358
Gln Ser Thr Tyr Gly Lys Asp Ser Ala Thr Lys Trp Thr Ala Tyr Trp
    335                 340                 345

aga aca ttc ttc ata gct gta gca gaa ctt ttt gga tac aat aac ggt     1406
Arg Thr Phe Phe Ile Ala Val Ala Glu Leu Phe Gly Tyr Asn Asn Gly
350                 355                 360                 365

gaa gaa tgg atg gtt gca cac ttc ctt ttc aaa aag aaa taa             1448
Glu Glu Trp Met Val Ala His Phe Leu Phe Lys Lys Lys
                370                 375

ataagccgaa acctagtctt tttatttgac tatttgagaa cggccttagg acaaaaaagc   1508

tgctacacga ggttgcaccc ttcaataatg ttgtatactt ttattagtta acttgtttta   1568

gttggttgct tgtctttatt tttccctgtt gtaatggtgt tgccactcca accttatttt   1628

atcttaaatt ttgggaaagt ccaattcaac cctcggaact tagggtcatg cacgattgca   1688

tgtgttctct agtccataaa ttttaaaatg tgcacttaag agcctttgta acgaaaatgg   1748

ttatgctcaa ggtagatgac catatatttg tgcacgctc                          1787


<210> SEQ ID NO 4
<211> LENGTH: 378
<212> TYPE: PRT
<213> ORGANISM: Glycine max

<400> SEQUENCE: 4

Met Ser Gln Asn Leu Asn Ile Val Asn Tyr Arg Leu Leu Ser Ser Ser
1               5                   10                  15

Leu Cys Leu Glu Thr Ile Ser Asn Thr Gly Thr Met Gln Leu Ala Tyr
```

```
            20                  25                  30

Glu Thr Val Val Lys Leu Met Leu Ala Ala Leu Glu Arg Asn Val Leu
        35                  40                  45

Pro Asp Val Ile Thr Arg Arg Leu Thr Arg Leu Leu Leu Ala Thr Arg
    50                  55                  60

Leu Arg Ser Ala Tyr Lys Pro Ser Ser Gln Leu Gln Leu Ser Asp Leu
65                  70                  75                  80

Leu Tyr Phe Ala His Ser Leu Gln Glu Met Pro Ile Ala Ile Asn Thr
                85                  90                  95

Asp Lys Pro Lys Ser Gln His Tyr Glu Leu Pro Thr Ala Phe Phe Lys
            100                 105                 110

Leu Val Leu Gly Asn Asn Leu Lys Tyr Ser Cys Cys Tyr Phe Ser Ser
        115                 120                 125

Ala Ser Met Thr Leu Asp Asp Ala Glu Glu Ala Met Leu Lys Leu Tyr
    130                 135                 140

Cys Glu Arg Ser Asn Leu Lys Asp Gly His Thr Val Leu Asp Val Gly
145                 150                 155                 160

Cys Gly Trp Gly Ser Leu Ala Leu Tyr Ile Ala Lys Asn Tyr Thr Asn
                165                 170                 175

Cys Arg Val Thr Gly Ile Cys Asn Ser Thr Thr Gln Lys Ala Tyr Ile
            180                 185                 190

Glu Glu Lys Cys Arg Asp Leu Gln Leu Gln Asn Leu Asn Ile Ile Val
        195                 200                 205

Ala Asp Ile Ser Thr Phe Glu Met Glu Thr Ser Tyr Asp Arg Ile Phe
    210                 215                 220

Ser Ile Glu Met Phe Glu His Met Lys Asn Tyr Lys Asp Leu Leu Lys
225                 230                 235                 240

Lys Ile Ser Lys Trp Met Lys Glu Asp Ser Leu Leu Phe Val His Tyr
                245                 250                 255

Phe Cys His Lys Ala Phe Ala Tyr His Phe Glu Asp Lys Asn Glu Asp
            260                 265                 270

Asp Trp Ile Thr Arg Tyr Phe Phe Thr Gly Gly Thr Met Pro Ser Ala
        275                 280                 285

Asn Leu Leu Leu Tyr Phe Gln Asp Asp Val Thr Val Thr Asn His Trp
    290                 295                 300

Leu Val Asn Gly Lys His Tyr Ala Gln Thr Ser Glu Glu Trp Leu Lys
305                 310                 315                 320

Arg Met Asp Gln Arg Met Thr Phe Ile Lys Pro Ile Met Gln Ser Thr
                325                 330                 335

Tyr Gly Lys Asp Ser Ala Thr Lys Trp Thr Ala Tyr Trp Arg Thr Phe
            340                 345                 350

Phe Ile Ala Val Ala Glu Leu Phe Gly Tyr Asn Asn Gly Glu Glu Trp
        355                 360                 365

Met Val Ala His Phe Leu Phe Lys Lys Lys
    370                 375
```

<210> SEQ ID NO 5
<211> LENGTH: 9349
<212> TYPE: RNA
<213> ORGANISM: Glycine max

<400> SEQUENCE: 5

```
gauaacggcu guuggaaaac aacccuuuac guuuaacgug aauaggaauc aaucacuauu      60

auuaauuuag uacuuucaac uugcaacucc cuuguaugug gaccuuugag uuccacguau     120
```

-continued

```
guauacaauc cauccauuug auacuugagu gcuacccuca uucuuauuaa agggucuuuu    180
uggguuguuc uauguaugca cauuuucaga uugcggcacu ugaauuaagg gaaaaggguu    240
gaaacuuacu gguuuuuguu acauaguaaa cuaaauagua gagagcaagg augagaguug    300
cagugguugg uagugggauu agugggguugg cuucagcuua ucuuuuggcc aaagggggag    360
ugaauguggu gcucuaugag aaggaggauu cguugggagg acaugccaag acugugaaug    420
uugaugggu ugauguugac cuuggcuuca uggucuucaa ucggguaagc auugcaaugg    480
uuuucuuuuu uuucucugau ucaauucuug aacacacuac uugugaggau uauuuuucuu    540
aguuauaacu uuuuucuuac gugaagauug aauugucaau uaauccuagc uucaaaauca    600
gucacacauu auccagaaca guaaaagggu gcugcuuuuu uaaugguuuu gguuuucaug    660
uaaacuuuga uucucuuaca uggaauguga guguuaagau gauguuguug gaguucucaa    720
gaguguucga gauagaauua uuagaaugag aauuauguuc agauuuucaa ggauuaauua    780
gaaaagauua gugaaaauau cauauucuag aagaggaauu aggaaaacuc acaauuucag    840
agacgaaaaa cauugcugaa uucagaaugu gguaugaagc cauuguuguu uuaauuccuu    900
guaauuuuau ucauuuagca aaggaaaagu augaacauau accguauuuu ggggugaagc    960
ugaaaauuag aaaaagauug agagaaauuu gaucgaugua auaaauaaca guaaaaacgu   1020
aaagagaaaa aaaaaugaaa augaggugaa agaaaaguua ggugauuugu auguuuaaua   1080
auaacauuuu agccuaaaua acuuauaaac agcugacuga ccucaggaga ggaauaauua   1140
acuuaguuaa uauuuugcag aauaacgaau uuauuguuug uaguguuggg ugaugcuuag   1200
ccacaccuga gcguuacuua uucuauuccc auucaacagc auacaugucc gguuugugag   1260
cauccauuuc uccauaauug acauuuaauu ucaguuuuuc aaaaccuuuu uuauaguaac   1320
uccuuccaag aauuaauuaa auauuaauug cccuuuuaaa aaauuaaaua uuaauuuauu   1380
agaaagaaaa uugucuuuua uuuaauauug aauuuauuac uuuaguguac uuuugaaaaa   1440
auuaaauauu aauugauuaa aaaaaauuau uuaucaauag cuauaaaaau guuaucuuuu   1500
uuccaaauuu ugauaauaaa aaaauaagaa aguuaaugua auuauuuaua ucauuuuaua   1560
uauaaauuuu uaaaauaaaa aaauaguauu uuuaaaauua ugaaaaagaa uauuucaaau   1620
caaacaaacu cucccgaaua guccauguga auguugaauc uaagaaugau uauuagacca   1680
agagacuaca aaagccagaa aguauacgcc auugcacaug aaaaggaaau auuuaguuac   1740
aauacuuuaa acauuuuauu cgcccaaaca cccacgugac ccacguaacu auauggauua   1800
aaaaaaaaac acucacguaa cuauacuuaa guugaucacc uaacuuuaca gcucuauggg   1860
ccccaccugu ggucaugaug uuuacuugug uaguuucuau caggcucaga cucguuugga   1920
cuucuagaua uugugaaccc gauggacaga acgcaacuaa aaaaaugaaa aaaauuguca   1980
aauugaagca uauauauaua uauauauaua uauauauaua uauauauaua uauauauaua   2040
uauauauauu uaugugcugg gcauuuaaug uaaccucaug ugaagcauca guauuaucag   2100
uuaaaauggg cauucaaugc uuuguuugug aaacugauug auuuggaccu gacuuguugu   2160
cccguacuca gcuguuuagg uuucuuuaua aaauuacaca auuuuaaaau ugaauauuaa   2220
uauaacuaca ugaauagauc caguuaacaa aaggacagag aagucaauuu cuauuuauuu   2280
uauaucaugg aaugauuaca gcagugcuug ugaggcuaua uauuuauuga cauuguaaca   2340
uggauuauug aacaggucac cuauccuaac auguuggauu uuuuugagaa ucuuggaguu   2400
gacauggaau caucagacau gucuuuuucu guuaguuuag acaaaggucg uggaugcgaa   2460
```

-continued

```
uggggaagca gaaaugguuu gucaagcuug uuugcacaga agaagaaugu acugaauccu   2520

uacuucuggc aaaugauaag ggaaauuguc aaguucaaag augauguuau uaggcaaguu   2580

gguaccuacu auaguugaag uuaaaucuuu cuuucagugu ucgauuguca gugaacuaag   2640

aaauaauaaa ucacauaaac aucuccaaau ugaugaugcc uuuuguuucu aagcuuugga   2700

uaaaauugua uacagaucag cuuuaauuuc ucuggccuga auauugaauu ugaacucaac   2760

agcaaaaagu ucaaaguugu gaugaacacu aauuacaagu guauaccgua uaguagucua   2820

cuuccuauug uccugaacag cugaacccug aucaauuagu uggcuuucuc uuuuccaauu   2880

cugcaaugca gcuaucuuga uaugcuugag aauaacccag auauugaccg caacgagccu   2940

cuaggggaau ucaucaaguc aagggguuac uccgaauuau uucagaaagc cuaucuugug   3000

aguucaaugg ugucaccugu auuuucuaua uauaucaauu uuaugcuaag uguguauauu   3060

uauaacaucc aaugccuaua gauuccaauu ugugguucua ucugguccug cucuucugaa   3120

ggaguuauga guuucucugc uuucucaguu cuuucauucu gucgcaacca ccaucuacuu   3180

cagguaguag cacaauugaa ucuuuuccag auuuauagug gcauauaauc uaguucuaua   3240

auccaaauaa cuaaagauua cuuauugauu cccuugaucc ucucugcagc ucuuuggcag   3300

accacagugg cuaacuguaa gauggcgcuc acaaacuuau guuaauaagg ugugauuugu   3360

ugauuaucau gcaaagucug uagaccugug ucacuuguga agcaguuuuc auugucacuc   3420

auacaagaga ucuuucagcu uaagcuguaa aucauuuuuu ugucauaaaa ucaggucaaa   3480

caagagcuug agagggaagg uagucaaaua auaacuaauc gugagguuca cuugguuucg   3540

acgacaucug aaaaagguga uaaagcaauc caucuguuac uuuuucaauu ccuuccucuu   3600

cagaaaggga aggugaauuc aauuggauug auuggcaugc acgucgcuuu uuuuucaaau   3660

aauaauuaua uauagacuau guaaugcugc ucuaguaaca auguuggaaa aauuauugca   3720

ggauguguug uguacugcaa ugaugguucu caagaaaugu augauggaug cauaauggca   3780

gugcaugcac cugaugccuu gcgauuauua ggagaugaag caacauauga ugagcgaaga   3840

auacucggag cuuuucaaua ugcuuacagg uaaaaucccu ucuaauauuu cuaauuguua   3900

gcuacccucc ucucagggaa uaagauaaca caaauuguag ugguuauauu uacaauaucu   3960

uuguguuauc auuuccguag acucaauaga guugacguug gauaguaaug cuuuuaucag   4020

cguguuauca aaccaaagga ugaaaacaau cuuaaauuua uugucuuagg accuauggca   4080

gaaauuuaag uauuauaagc cuggaggcaa ugguauacgu uuaucucauc acauauauau   4140

uaaugacaaa aauaugugaa guugcuaaaa ucaagaaucu uuuuucaucu auauucaaau   4200

aaguccaaau gcacaauuau ucuuugaucu guauuggcag ugauauuuuu cuucaucgug   4260

acaaaaauuu aaugccccaa aacccagcag cauggagugc auggaauuuu cuugguagua   4320

acaacaacaa aguuugucua acauacugga ucaauauucu ucagguuggc aaauuuuaua   4380

uaaaugcauu gaucauaacu gaacugucuu gggccuauuc uaucuaaaga ggguaaugga   4440

caaaauuguu gguuaauauu uauucuaauu ugcagaauau uaaagagaca agucaacccu   4500

uucuuguaac ucucaaucca gaccauauac cagaaaauac cuugcuaaag uggucaacug   4560

gccauccagu cccaucaguu gcugcauuca aagcuucauu agagcuugac cauauucaag   4620

ggaaaagaaa aaucugguuu ucaggagcau accaagguac auuccugcuu auuguauuga   4680

caaucaagau aaacuacuaa uaaucaugac aguacuagcu uccaugaacu cucucaugcc   4740

uacuaaauua uguauaucua aucuccauuu uuuuuagaaa caaccuuugu uagguugagg   4800

aauuuauaua cuucaaauau accaagugau cuaaccauau auuugugcuu uuucagguua   4860
```

-continued

```
uggauuucau gaagauggau uuaagguagu uaaagcuaag uauauaauga aagaagaaau   4920
auaguuuuaa cugaaaaaua uuucuuugaa gaguuuccuu aaaguggaaa ugucuugagg   4980
caauuaauuu aauuacaaau ugucaccaac ccguugaaau gaaacaaaac uuaacuauac   5040
gauugaacuu ucaggcuggc augaucgcag cucauggcau ucuaggaagc ugcugugccc   5100
uucagaccaa cccaaaacac augguaccuu cuuggaagga acugggagca cgcauuuuug   5160
ugacuagauu ccugaguugc uauaucacua cugguuguuu aaugugagac aucuagcagu   5220
aagaauucuc ucaaaaaaca aaaaaguauc auaaucauau gcuugauguu aauauaccaa   5280
gauguaucag gauaguagug aacacaccua aguacuuugg aauuauacaa gcuucaguua   5340
cucuuucaag uugguaauau auucauucaa uacguaugca aguagaauug gcauucauuu   5400
agacacagga ucuuuacuug uaauuuggaa aauuguacaa agcuuaucau uuacuuguau   5460
gcucgaagac caaaaauuga augaggguga uuccaaaaac aauagaggau cuauuggaau   5520
ugcuauuuau gaaaacaaua auaaacauuu acuuugauau caugcucuag acuguucuua   5580
gcauaauuuu uuuuuuauu ucaaagcuug acaauaacaa gguccaaaau auaucaucua   5640
cuucaucuuc uauggauuug acugguaaaa aaugauucaa guuaauggua cauuuaccuu   5700
gagguguaca gguuacugga agagggagga acaauguuca ccuuugaggg aacugggaaa   5760
aacuguggcuc ugaagagugu uuugagggac cacgauccac aauuuuauug gaagguauau   5820
acuuuuaaau uucacaugaa cuaugauuau ugauucaugu cauucuagcu gcggaaguga   5880
caagauaugc uuaucuuugu caaugcaacu cuaaaauuaa guagcuagca aggagcuaaa   5940
acuaaucauu uguacguaua uuucagguga ugacacaggc agauuuaggc cuugcagaug   6000
cauauaucaa uggggacuuu ucauuuguug auaaagauga aggucucuug aaucuuauuu   6060
ugguaagcau ucucaucuga aucuuucagu gaguugucuc uuugggacuc uacacuucaa   6120
uauaccaugg uauuuuuacu gcagauucuc auagccaaca gagauucaaa ugcauccaac   6180
ucaaaacuga agaagaauag guaaguggau auguaaguug aagccuacac uuacauauua   6240
acuguaucgg cauaucaaac uuuuuuuguu uuaugccuuu aggggguuggu ggacacccgu   6300
uuucuuuacg ucugcuuuga caucugcaaa guucuucaug gaucauguuu caaggcgaaa   6360
uacucucacg caggcucgca ggaacaucuc uaggcauuau gaucugguau gagcacauua   6420
uccaacaaua uaaaguagug ugagcauaua acuaguuaca cacaaucaca aaaaagucaa   6480
augaaagauu cuuuaucaag agagauaacu caaauauuug aagacugagu uuacucucaa   6540
aauguaugua ccugucgaag gaauaaugaa gaggcucgga auaggaaaua ucuuccaaga   6600
acuauguuac agacuguagu caugcauagg agauccauga agacuguaga cuacauacau   6660
gaauaacaug gacuggaucu uucuuuugcc uugguguaac augaauauag acauacucaa   6720
ugcuucgguu acaguuuaua gauugugaau agcauauaua caguuuguua uaccacaaua   6780
uuucagcuag aaauauauau ugcuugacaa agaaguguaa uugaauuucu caauugcucu   6840
cucuuuugug uuaacauuuu auuuaugcau auuccauagu uuuuugagac cugacacuaa   6900
augaacagaa gcuguaauuu uucuuuggcc uguuucuaga gcaaugaccu cuuugcgacu   6960
uucuuggaug aaacaaugac auauucaugu gcaguguuca aggcaagaac aacaacuauc   7020
ugaugcuuga gucagaauuu cacauuauaa auauuucucc aguuucugga gcagcgcugg   7080
uuaauacucu uccuucuuuu uuguuaaacu auuugguaga auaaagauga agacuugaaa   7140
gaugcacaaa agagaaaaau cucucuccug auugaaaaag uaagugccuu ugauugcuau   7200
```

-continued

```
cuuauuacua guauuuuagu uguuaucuua caaaaggucu uauaagaacu uuccuucaau   7260
aaaucaaggc uagaauagau aagacacaug aaauucuuga gauuggaugu ggaugggaa    7320
guuuagccau ugaaguuguc aaacaaaccg gcugcaaaua cacugguauc acuuugucug   7380
aggagcaacu gaaacuugca gaacaaagag uuaaagaugc ugggcuucag guauuuacaa   7440
gcucauuuau uuucacaguu ucacgaauuu cauaacauaa aauaugaugg auuuuuuuau   7500
gaaauuugga aaagcuaaau gcaauguuag aaauucucaa gugaauucau guuauuuuau   7560
ucaugguucc aggaccgcau caauuuuguu cuaugcgacu aucgccaauu gcccaagaca   7620
uauaaaauacg auaggauuau aucuugguga gcuauuuauc auuuaauuua cuuugcagac  7680
uaguugcaau uuuccaacac auugcauaac uuguauaagc auacuucagu gaaaugauag   7740
aagcuguugg ucaugaauac auggaagagu ucuuuggcug uugugaauca guauuggcgg   7800
auaauggacu ucuuguucuc caggguguuug auagauuauu acuuuuauua ucuguauggu  7860
ucuuuuuuau guaauguuua gauuaaaaaa cuuuauacag ggcaugcuau acaaaggaaa   7920
caagaacaug cacauuauuu uugguauuua aauuacugcu aacuauugaa aagaugguua   7980
uuuucuauag uucauaucaa ucccggauga gcguuaugau gaauauaggc gcaguucuga   8040
uuuuauaaag gaauauauau uuccaggagg uugccuaccc ucucuaagua ggauaacauc   8100
ugccauggca gccacaucca gacuauggua caauuuacau cuaaauagag uuuuaucaau   8160
gagcuuuccc uucauucuuu ucucuuacag aaaagaauuu ucuuaaaugc agcguggagc   8220
acguugaaaa cauagguauu cauuacuacc aaacacucag augcuggaga aaaaacuucu   8280
ugaaaaggca gaaguaugcu auuaauuuga uugaaacuca cuuuuguaug uuaaauucaa   8340
guaacuacuu acaacagcua auuauuaugu uuauuuuugu gcugacagug aaauuuuggc   8400
ucucggauuc aaugaaaaau uuaucaggac augggaauac uauuuugauu acuguggugc   8460
agguuuuaag ucacucacac uagggaauua ucagguauau uacaguuacu guuacaaucu   8520
uggaguaacu uuauccauua aacucacuag uuaagaugac uuggcauagc cuuauguguc   8580
auucuuaugu gcuggccauc auccuacaag aaaguaccaa ccuaaacuua gcuauuaugu   8640
aauacugaca acagcaaucu agucuucucu caauggucaa agucugccac augaauuaaa   8700
ccacguuaug guaacaaagu uaguguuaau uuugcuauca uguaaucuac caguaaaaua   8760
ucauuuucua gaaaaacaac ccaaauuucu guaacaaacu ugauguuaau uuugcugaaa   8820
uuuagguuaa ccuuugagua cuugauuaac aagauauucu auucaacagu gacacuuguc   8880
aaaauguaac auguugcucg caguugcgau uguaacaaaa caaguauaua auauguuuua   8940
uguaccaugu agguggguuuu cucacgcccu gguaacguuc cugcauuagg cgauccauac  9000
aaaagcuaga ccaaaaccag uugacagaac aagccucaca cauucuacca aagugcauua   9060
caugauggug ccaccaugua ucuccuuucu ugauaaucuc gaaguaauuu uuuugucaau   9120
auagaucucu uguacauugu uaaaauagag gagcugaaau gugcuguuuu gccguggcaa   9180
acagcaagau uggugagaag uuuuucucac aaaugauauu uuuuuaaaaa ggaacaagcu   9240
uauugaugcc caaaaacaaa uaacucauua aauuucugug uaacuuuuua ucccguagcu   9300
gacaaguaaa cauauaauau uaucccuauu uugcuaauuu ucauuaucu                 9349
```

<210> SEQ ID NO 6
<211> LENGTH: 25
<212> TYPE: DNA
<213> ORGANISM: Artificial
<220> FEATURE:
<223> OTHER INFORMATION: Synthetic DNA

<400> SEQUENCE: 6
actatacgat tgaactttca ggctt 25

<210> SEQ ID NO 7
<211> LENGTH: 22
<212> TYPE: DNA
<213> ORGANISM: Artificial
<220> FEATURE:
<223> OTHER INFORMATION: Synthetic DNA

<400> SEQUENCE: 7
gcttcctaga atgccatgag ct 22

<210> SEQ ID NO 8
<211> LENGTH: 22
<212> TYPE: DNA
<213> ORGANISM: Artificial
<220> FEATURE:
<223> OTHER INFORMATION: Synthetic DNA

<400> SEQUENCE: 8
tcgtatttat atgtcttggg ca 22

<210> SEQ ID NO 9
<211> LENGTH: 18
<212> TYPE: DNA
<213> ORGANISM: Artificial
<220> FEATURE:
<223> OTHER INFORMATION: Synthetic DNA

<400> SEQUENCE: 9
ggaccgcatc aattttgt 18

<210> SEQ ID NO 10
<211> LENGTH: 25
<212> TYPE: DNA
<213> ORGANISM: Artificial
<220> FEATURE:
<223> OTHER INFORMATION: Synthetic DNA

<400> SEQUENCE: 10
agaaaaatct ctctcctgat tgaaa 25

<210> SEQ ID NO 11
<211> LENGTH: 25
<212> TYPE: DNA
<213> ORGANISM: Artificial
<220> FEATURE:
<223> OTHER INFORMATION: Synthetic DNA

<400> SEQUENCE: 11
agtaataaga tagcaatcaa aggca 25

<210> SEQ ID NO 12
<211> LENGTH: 20
<212> TYPE: DNA
<213> ORGANISM: Artificial
<220> FEATURE:
<223> OTHER INFORMATION: Synthetic DNA

<400> SEQUENCE: 12
tcatcaccag gagactcacg 20

<210> SEQ ID NO 13

-continued

```
<211> LENGTH: 19
<212> TYPE: DNA
<213> ORGANISM: Artificial
<220> FEATURE:
<223> OTHER INFORMATION: Synthetic DNA

<400> SEQUENCE: 13

aagttgggag gagggtttg                                                  19
```

SOYBEANS HAVING LOW FURAN FATTY ACID CONTENT

TECHNICAL FIELD

The present invention relates to a modified soybean having reduced furan fatty acid content in the oil/fat contained in the soybean, and the like.

BACKGROUND ART

Soybean is a world's major source of edible oils/fats of plant origin. Since the composition of fatty acids contained in oils/fats has a direct influence on the quality of the oils/fats, modification of fatty acid compositions is a major issue in the breeding of soybeans.

In general, edible oils/fats are degraded by light, heat, and the like, and develop an odor that can cause a flavor problem. In particular, soybean oils/fats produce a peculiar odor called "light-induced odor (or "light exposure odor")" in the presence of light or "heat-induced odor" caused by heat cooking or the like. Therefore, it has been pointed out that edible oils/fats containing a high percentage of soybean oils/fats, or food products and the like containing soybean oils/fats cannot be guaranteed to have acceptable quality (Patent literature 1). A degradation product of "furan fatty acid" in the fatty acid composition of the soybean oil/fat is thought to be a cause of these light-induced odor and heat-induced odor.

CITATION LIST

Patent literature 1: Japanese Patent Publication No. 4290222

SUMMARY OF INVENTION

Under these circumstances, it has been desired to develop a modified soybean having a reduced furan fatty acid content (production amount of furan fatty acid) in the oil/fat contained in the soybean.

The present invention was made in consideration of the above circumstances and provides the following modified soybeans, and the like.

(1) A modified soybean in which the content ratio of furan fatty acid in the oil/fat contained in the soybean has been reduced by genetic mutation.

(2) The soybean according to (1) above, wherein the content ratio is 0 ppm by mass or more and 20 ppm by mass or less.

(3) The soybean according to either one of (1) and (2) above, wherein the furan fatty acid is 3,4-dimethyl-5-pentyl-2-furannonanoic acid.

(4) The soybean according to any one of (1) to (3) above, which has a mutation introduced into Glyma20g34340 gene and/or Glyma04g05690 gene.

(5) The soybean according to (4) above, wherein the mutation introduced into the gene is any of the mutations selected from the group consisting of missense mutation, nonsense mutation, frameshift mutation, and null mutation.

(6) The soybean according to either one of (4) and (5) above, wherein the mutation introduced into the Glyma20g34340 gene is:

(i) a mutation of a nucleotide in the codon encoding the 410th amino acid residue of the protein encoded by the gene:

(ii) a mutation of a nucleotide in the codon encoding the 688th amino acid residue of the protein encoded by the gene; or (iii) a mutation of a nucleotide present at the boundary between the 17th exon and intron of the gene.

(7) The soybean according to (6) above, wherein the mutation of (i) above is a mutation where a codon of glycine is replaced with a codon of aspartic acid.

(8) The soybean according to (7) above, wherein the mutation of (i) above is a mutation where the 1519th nucleotide, G (guanine), in the cDNA of the Glyma20g34340 gene is replaced with A (adenine).

(9) The soybean according to (6) above, wherein the mutation of (ii) above is a mutation where a codon of aspartic acid is replaced with a codon of asparagine.

(10) The soybean according to (9) above, wherein the mutation of (ii) above is a mutation where the 2352nd nucleotide, G (guanine), in the cDNA of the Glyma20g34340 gene is replaced with A (adenine).

(11) The soybean according to (6) above, wherein the mutation of (iii) above is a mutation where the 7180th nucleotide, G (guanine), in the mRNA precursor of the Glyma20g34340 gene is replaced with A (adenine).

(12) The soybean according to either one of (4) and (5) above, wherein the mutation introduced into the Glyma04g05690 gene is a mutation of a nucleotide in the codon encoding the 64th amino acid residue of the protein encoded by the gene.

(13) The soybean according to (12) above, wherein the mutation is a mutation where a codon of arginine is replaced with a codon of cysteine.

(14) The soybean according to (13) above, wherein the mutation is a mutation where the 483rd nucleotide, C (cytosine), in the cDNA of the Glyma04g05690 gene is replaced with T (thymine).

(15) The soybean according to any one of (1)-(14) above, which is a modified Fukuyutaka soybean.

(16) LF65 soybean whose accession number is FERM BP-22392.

(17) 16SN279 soybean whose accession number is FERM BP-22413.

(18) An ingredient for food products, feed products or pharmaceutical compositions, the ingredient comprising the soybean according to any one of (1)-(17) above or a processed product thereof.

(19) A food product, feed product or pharmaceutical composition comprising the ingredient according to (18) above.

(20) A soybean oil/fat extracted from the soybean according to any one of (1)-(17) above.

(21) A food product, feed product or pharmaceutical composition comprising the soybean oil/fat according to (20) above.

(22) A method for producing a modified soybean, the method comprising crossing the soybeans according to any one of (1)-(17) above with each other, or crossing said soybean with other soybean species.

Advantageous Effects of Invention

The present invention can provide a modified soybean having a reduced furan fatty acid content (production amount of furan fatty acid) in the oil/fat contained in the soybean. An edible oil/fat derived from this modified soybean and food products containing this edible oil/fat are different from those containing conventional soybean oils/fats in that the unpleasant light-induced odor peculiar to soybean oils/fats is suppressed, and the heat-induced odor caused during heat cooking, etc., especially the irritating odor originating from soybean oils/fats, is suppressed. Furthermore, in the edible oil/fat derived from the modified soybean, the increases in viscosity, color tone and oxidation caused during heating are more suppressed than those in conventional soybean oils/fats. In addition, food products and the like containing the modified soybean or a processed product of said modified soybean have a good flavor with a suppressed beany smell. Therefore, the above modified soybean is highly useful and practical.

DESCRIPTION OF EMBODIMENTS

Figure 1:
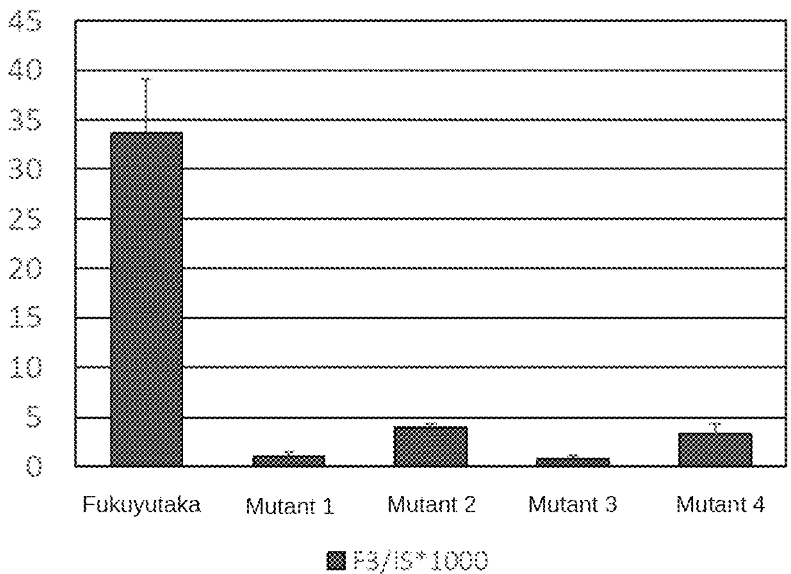
FIG. 1 Figure showing the furan fatty acid contents (F3/internal standard (IS)×1000) of Fukuyutaka (original variety) and four mutant lines (Mutants 1-4) (corresponding to the results shown in Table 1 in Example 1).

Hereinafter, the present invention will be described in detail. The scope of the present invention is not bound by these descriptions, and the present invention may be implemented with suitable modifications other than those described in the following examples, provided that the purpose of the present invention is not impaired. The present specification incorporates the specification of Japanese Patent Application No. 2021-007795 (filed on Jan. 21, 2021 (Reiwa 3)) in its entirety, which serves as the basis for claiming priority of this application. In addition, all publications cited herein, such as prior art literature, patent application publications, patent publications and other patent literature, are incorporated herein by reference.

1. Modified Soybean

As described above, the present invention provides a modified soybean in which the content ratio of furan fatty acid in the oil/fat contained in the soybean has been reduced by genetic mutation (hereinafter sometimes referred to as "the soybean of the present invention" or "the modified soybean of the present invention").

According to the present invention, a "soybean" refers to the whole or a part of an individual soybean plant, which includes an individual plant as well as a partial structure such as an organ (seed, etc.) of the individual plant, and a cell or cell organelle derived from the individual plant.

According to the present invention, "genetic mutation" may be, but is not limited to, a mutation by genetic recombination (modification of genetic characteristics by genetic recombination technique) or a non-genetic recombination type mutation, for example, random mutation or genome editing. Random mutation is not particularly limited and, for example, a mutation by treatment with chemicals (e.g., ethyl methane sulfonate (EMS), nitroso methyl urea, nitroso methyl urethane, etc.) or UV irradiation, a mutation introduced by employing Diversify™ PCR method, Error-prone PCR method, Rolling Circle Amplification (RCA) method, Error-prone RCA method, or any of various known random mutagenesis kits can be employed as appropriate.

The mutation introduced into the gene by any of the above methods may be, but is not limited to, any one mutation selected from the group consisting of missense mutation, nonsense mutation, frameshift mutation, and null mutation, or a combination of two or more of these mutations. A "missense mutation" refers to a mutation where a change or substitution of a nucleotide in a codon of a nucleic acid sequence changes the type of amino acid encoded by that codon. A "nonsense mutation" refers to a mutation where a change or substitution within a codon of a nucleic acid sequence changes that codon into a stop codon, so that the ORF region 3' to the codon is no longer translated. Nonsense mutations are also called as termination mutations. A "frameshift mutation" refers to a mutation where an insertion or deletion of a nucleotide results in a shift of the codon reading frame in the region 3' to the insertion or deletion site. Furthermore, a "null mutation" refers to a mutation where the nucleotide sequence encoding the protein is completely deleted, or where the functional protein cannot be expressed even if the nucleotide sequence is present.

According to the present invention, the soybean before the genetic mutation (the original soybean of the modified soybean of the present invention) may be a soybean variety that has not undergone any modification of the genetic characteristics by genetic recombination or the like (i.e., wild soybean), or may be a soybean variety that had undergone breeding or the like by introducing some kind of modification of the genetic characteristics into such soybean variety, where examples of such soybean variety include, but are not limited to, "Fukuyutaka", "Toyoshirome", "Murayutaka", and "Bay".

The modified soybean of the present invention is characterized in that the content ratio of furan fatty acid in the oil/fat contained in the soybean has been reduced, where this content ratio is, for example, preferably 0 ppm by mass or more and 20 ppm by mass or less, and may be 0 ppm by mass or more and 15 ppm by mass or less, 0 ppm by mass or more and 10 ppm by mass or less, 0 ppm by mass or more and 5 ppm by mass or less, 0 ppm by mass or more and 3 ppm by mass or less, 0 ppm by mass or more and 1 ppm by mass or less, and even 0 ppm by mass.

The reduced furan fatty acid in the modified soybean of the present invention is preferably, but not limited to, 3,4-dimethyl-5-pentyl-2-furannonanoic acid (also referred to as "F3"), which is represented by the following structural formula.

[Chemical formula 1]

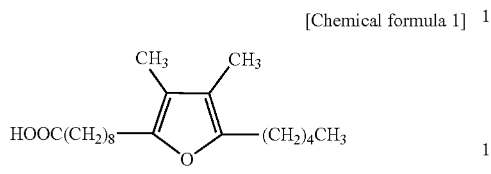

The modified soybean of the present invention is preferably one that has a mutation introduced into Glyma20g34340 gene and/or Glyma04g05690 gene (or one containing such mutation). Herein, "introduced with a mutation" or "containing a mutation" means that the mutated gene is retained in the soybean cell, and preferably the mutated gene is retained in the genome of the soybean. The mutation may also be a loss-of-function mutation in the above gene.

For details of the above Glyma20g34340 gene and Glyma04g05690 gene, for example, "Phytozome" (https://phytozome.jgi.doe.gov/pz/portal.html) in the website of "Joint Genome Institute (JGI)" (https://jgi.doe.gov/), which is one of the various publicly known databases, provides genome sequence information of the genes, cDNA nucleotide sequence information of the genes, the amino acid sequence information of the proteins encoded by the genes, and the information on the nucleotide sequence regions (CDSs) coding for the amino acid sequences.

According to the present invention, the nucleotide sequence of the cDNA of the above Glyma20g34340 gene is represented by SEQ ID NO: 1 and the amino acid sequence of the protein encoded by the Glyma20g34340 gene is represented by SEQ ID NO: 2. The nucleotide sequence of the mRNA precursor of the Glyma20g34340 gene (sequence whose representation of the genomic DNA sequence has been converted to that of RNA (thymine (T) converted to uracil (U)) is represented by SEQ ID NO:5.

Note that the gene name of the Glyma20g34340 gene is indicated as "Glyma.20G201400.1" or "Glyma.20G201400" in version Wm82.a2.v1 of the above database (Phytozome).

Meanwhile, the nucleotide sequence of the cDNA of the above Glyma04g05690 gene is represented by SEQ ID NO: 3 and the amino acid sequence of the protein encoded by the Glyma04g05690 gene is represented by SEQ ID NO: 4.

Note that the gene name of the Glyma04g05690 gene is indicated as "Glyma.04G054100.1" or "Glyma.04G054100" in version Wm82.a2.v1 of the above database (Phytozome).

Examples of the mutation introduced into the above Glyma20g34340 gene include, but are not limited to, the following genetic mutations (i)-(iii).

(i) A mutation of a nucleotide in the codon encoding the 410th amino acid residue of the protein encoded by the gene.

Here, the mutation of (i) above is preferably, for example, a mutation where a codon of glycine is replaced with a codon of aspartic acid. Specifically, it may be a mutation where the 1519th nucleotide, G (guanine), in the cDNA (SEQ ID NO: 1) of the Glyma20g34340 gene is replaced with A (adenine).

(ii) A mutation of a nucleotide in the codon encoding the 688th amino acid residue of the protein encoded by the gene.

Here, the mutation of (ii) above is preferably, for example, a mutation where a codon of aspartic acid is replaced with a codon of asparagine. Specifically, it may be a mutation where the 2352nd nucleotide, G (guanine), in the cDNA (SEQ ID NO: 1) of the Glyma20g34340 gene is replaced by A (adenine).

(iii) A mutation of a nucleotide present at the boundary between the 17th exon and intron of the gene.

Here, the mutation of (iii) above is, for example, a mutation of a nucleotide that demarcates the boundary with the intron located immediately after the 17th exon of the gene, preferably a mutation introduced into at least one or more nucleotides of "GU" (7180th-7181st) and "AG" (7267th-7268th), which designate the boundary of the intron specified by the 7180th-7268th nucleotides in the mRNA precursor of the Glyma20g34340 gene (SEQ ID NO:5) and more preferably a mutation where the 7180th nucleotide, "G" (guanine), in the mRNA precursor (SEQ ID NO:5) is replaced with "A" (adenine).

An example of the modified soybean of the present invention in which the mutation of (i) above has been introduced into the Glyma20g34340 gene include a soybean variety of the "#65" line (hereinafter also referred to as "LF65"), where this soybean variety has been deposited at the International Patent Organism Depositary, Biological Resource Center, National Institute of Technology and Evaluation (Room No. 120, 2-5-8 Kazusakamatari, Kisarazu-shi, Chiba, 292-0818, Japan) under the deposition number "FERM BP-22392", as of Jul. 16, 2020. Examples of the modified soybean of the present invention into which the mutation of (ii) above has been introduced include a soybean variety of the "16SN253" line and examples of the modified soybean into which the mutation of (iii) above has been introduced include a soybean variety of the "16SN693" line.

Meanwhile, examples of the mutation introduced into the above Glyma04g05690 gene include, but are not limited to, a mutation of a nucleotide in the codon encoding the 64th amino acid residue of the protein encoded by the gene.

Here, this mutation may preferably be, for example, a mutation where a codon of arginine is replaced with a codon of cysteine. Specifically, the mutation may be a mutation where the 483rd nucleotide, C (cytosine), in the cDNA (SEQ ID NO:3) of the Glyma04g05690 gene is replaced with T (thymine).

An example of the modified soybean of the present invention where the above mutation has been introduced into the Glyma04g05690 gene include a soybean variety of the "16SN279" line (hereinafter also referred to as "16SN279"), where this soybean variety has been deposited at the International Patent Organism Depositary, Biological Resource Center, National Institute of Technology and Evaluation (Room No. 120, 2-5-8 Kazusakamatari, Kisarazu-shi, Chiba, 292-0818, Japan) under the deposition number "FERM BP-22413", as of Jan. 14, 2021.

2. Use

The present invention provides an ingredient for food products, feed products or pharmaceutical compositions (or medicines), which contains the aforementioned modified soybean of the present invention or a processed product thereof. Also provided by the present invention is a soybean oil/fat extracted from the aforementioned soybean of the present invention. In addition, the present invention also provides a food product, a feed product or a pharmaceutical composition (or medicine) containing the above ingredient or the above soybean oil/fat.

A "processed product of soybean" refers to a soybean that has been subjected to treatments such as enzymatic treatment, powdering, drying, heating, freezing, or refinement. Specific examples of the processed product of soybean include full-fat soy flour, non-fat soy flour, and soybean protein.

"Food products" refer to products that are eaten for the purpose of nutrient intake or palatability. Soybeans have long been consumed as a food. The soybean of the present invention may be eaten as a fresh food like edamame, as a fermented food product like natto, or as a processed food product like dried beans, miso, soy sauce, bean curd, bean curd skin, soy milk, and soybean flour. While food products that can use the above-mentioned processed product of soybean as an ingredient are not limited, they may be, for example, food products in which some or all of the meat contained in processed meat products is replaced with a processed soybean product, such as hamburger steak, patties, Chinese dumplings, fried-chickens, sausages, croquettes, nuggets, shumai, pork cutlets, chicken fillets, minced meat, meat ingredients in rice products like fried rice, and meat ingredients in instant noodles, and bakery foods such as cookies, cakes, doughnuts, and breads. While the use of the soybean oil/fat is not limited, it may be used for, for example, deep frying oil, stir frying oil, rice cooking oil, and pouring oil. Examples of food products containing the soybean oil/fat include deep-fried foods, stir-fried foods, rice foods, rice crackers, noodles, seasonings such as mayonnaise and dressings, powdered oils/fats, and processed oil/fat food products such as margarine and shortening. Since the soybean of the present invention has a reduced amount of furan fatty acid in the soybean oil/fat and thus has the light-induced odor and heat-induced odor suppressed, the consumer is expected to be more comfortable for its use in foods and beverages. The soybean of the present invention may also be used as an ingredient in supplements, health functional food products, and food products for specified health uses.

"Feed products" refer to those fed to reared animals, where "reared animals" include livestock, poultry, farmed fish, and pets. Soybean is widely used in livestock and poultry feeds for cattle, pigs, chickens, and the like, and in pet foods.

"Pharmaceutical compositions" (or "medicines") refer to those that are administered to a subject, such as a human or animal, to diagnose, treat, or prevent a disease in the subject, and may include quasi-drugs as long as such efficacy is obtained. Isoflavones contained in soybeans are known to exhibit an agonist effect on estrogen receptors and are used as a therapeutic drug for osteoporosis.

3. Crossing

A novel modified soybean that has the characteristics of the soybean of the present invention can be produced (bred) by crossing the soybeans (soybean species) of the present invention with each other or by crossing the soybean (soybean species) of the present invention with other soybean species. The novel modified soybean obtained in this way also has the characteristic of reduced content ratio of furan fatty acid in the oil/fat contained in the soybean, as described in section 2. above, and the like.

Preferably, the soybean species of the present invention can be crossbred with other soybean species to produce a novel modified soybean species in which a mutation (loss-of-function mutation, etc.) has been introduced into the Glyma20g34340 gene and/or Glyma04g05690 gene. For example, by crossing the soybean species of the present invention with other soybean species that are tolerant to certain pests and/or growing conditions, a novel soybean species can be produced that has a reduced furan fatty acid content in the oil/fat contained in the soybean and that is tolerant to certain pests and/or growing conditions.

According to the present invention, "crossing" refers to a crossing between two individuals with different genetic compositions, which results in the formation of a hybrid. Backcrossing is preferred as the method of crossing. In order to achieve a reduced furan fatty acid content in the novel soybean species obtained by crossing, it is necessary to backcross the novel soybean species with the soybean species of the present invention to obtain a homozygote of the Glyma20g34340 gene mutation or the Glyma04g05690 gene mutation. "Backcrossing" is a method of crossing an offspring of a mutant parent A and a non-mutant parent B (existing soybean variety such as Fukuyutaka) with the parent B (existing soybean variety such as Fukuyutaka) to obtain an offspring that retains the mutated gene and that has the characteristics of the parent B.

4. Screening Method

The soybean of the present invention preferably has a mutation in the Glyma20g34340 gene and/or Glyma04g05690 gene, so by detecting the mutation in either of these genes (or both genes), soybeans can be screened for those with reduced furan fatty acid content in the oil/fat contained in the soybean.

A method for detecting the mutated gene may be a method comprising the steps of:

(a) performing amplification treatment and/or hybridization treatment for the Glyma20g34340 gene and/or Glyma04g05690 gene of the tested soybean, using an oligonucleotide probe containing the nucleotide sequence of the mutated site of the Glyma20g34340 gene and/or Glyma04g05690 gene of the modified soybean of the present invention, and/or oligonucleotide primers prepared such that the mutated site is included in the amplified fragment when at least one of the nucleotide sequence of said gene and its complementary sequence is amplified; and (b) detecting the mutated site by analyzing the treated product.

Specific examples of such detection method include, but are not limited to, known methods such as PCR method, TaqMan PCR method, sequencing method, and microarray method, and especially Invader assay and TILLING method when the loss-of-function mutation is a single nucleotide polymorphism (SNP).

In the case of the PCR method, it is preferable to create primers such that the 3' end portion has a sequence complementary to the nucleotide sequence of the mutation site. By using the primers designed as such, if a sample template has a mutation, the primers will completely hybridize to the template and the polymerase elongation reaction will proceed, but if the template does not have a mutation, elongation reaction does not occur because of the mismatch of the nucleotides at the 3' end of the primers with the template. Therefore, when PCR amplification is performed using such primers, and the amplified product is analyzed by agarose gel electrophoresis or the like, it can be judged that the sample template has a mutation if an amplified product of a predetermined size can be confirmed whereas the template does not have a mutation if the amplified product is not present. For PCR and agarose gel electrophoresis, see below: Sambrook, Fritsch and Maniatis, "Molecular Cloning: A Laboratory Manual," 2nd Edition (1989), Cold Spring Harbor Laboratory Press.

The TaqMan PCR method is a method that utilizes a fluorescently labeled allele-specific oligo and PCR reaction by Taq DNA polymerase (Livak, K. J. Genet. Anal.

The sequencing method is a method of analyzing the presence or absence of a mutation by amplifying the region containing the mutation by PCR and sequencing the DNA sequence using Dye Terminator or the like (Sambrook, Fritsch and Maniatis, "Molecular Cloning: A Laboratory Manual" 2nd Edition (1989), Cold Spring Harbor Laboratory Press).

The DNA microarray has one end of nucleotide probes fixed on a support in an array, which includes a DNA chip, Gene chip, microchip, bead array, and else. Examples of the DNA microarray assay using DNA chips or the like include GeneChip assay (Affymetrix: see U.S. Pat. Nos. 6,045,996, 5,925,525, and 5,858,659). The GeneChip technology utilizes a miniaturized high-density microarray of oligonucleotide probes attached to a chip.

The Invader assay is a method that combines hybridization of two types of reporter probes and one Invader probe specific for each allele of a genetic polymorphism (e.g., SNP) to template DNA, with cleavage of DNA with Cleavase enzyme which has a specific endonuclease activity of recognizing and cleaving the DNA structure (Livak, K., J. Biomol. Eng. 14, 143-149 (1999): Morris T. et al, J. Clin. Microbiol. 34, 2933 (1996): Lyamichev, V. et al., Science, 260, 778-783 (1993), etc.).

The TILLING (Targeting Induced Local Lesions IN Genomes) method is a method of screening for a mutant mismatch in genomes of a mutagenized population by PCR amplification and CEL I nuclease treatment. CEL I nuclease is an endonuclease that specifically cleaves the mismatch portion of double-stranded DNA. The above PCR product will have a mismatch portion if the sample contains a mutation in the Glyma20g34340 gene and/or Glyma04g05690 gene, but will not have a mismatch portion if no mutation is contained. Thus, if the mutation is present, the mismatched pair site in the PCR product will be cleaved, and if the mutation is not present, the PCR product will not be cleaved. Therefore, the presence or absence of the mutation can be easily confirmed by analyzing the CEL I nuclease-treated PCR product by agarose electrophoresis or the like and comparing the lengths of the nucleic acid sequences. For more information on CEL I nuclease, the following literature is available: Oleykowski et al., Nucleic Acids Research, vol. 26, No. 20, 4597-4602 (1998).

In the mutation detection methods exemplified above, an oligonucleotide prepared to contain a mutated site in the Glyma20g34340 gene and/or Glyma04g05690 gene is used as the probe or primer. Thus, the present invention also provides an oligonucleotide prepared to contain a mutated site in the Glyma20g34340 gene and/or Glyma04g05690 gene.

In a case where a mutation in the Glyma20g34340 gene and/or Glyma04g05690 gene is detected by Invader assay, the primer or probe used is designed such that the SNP site is located at the 3' or 5' end of the nucleotide sequence of the primer or probe, at the 3' or 5' end of the complementary sequence, or within 4 nucleotides, preferably within 2 nucleotides, of the 3' or 5' end of the former two sequences (i.e., the primer or probe, or complementary sequence). Alternatively, the primer or probe is designed such that SNP is located in the middle of the entire length of the nucleotide sequence of the oligonucleotide. The "middle" refers to the region in the middle part where the number of nucleotides toward the 5' end and the number of nucleotides toward the 3' end from the nucleotide of the SNP are approximately equal, and if the oligonucleotide has an odd number of nucleotides, the "middle" preferably refers to five nucleotides in the middle part, more preferably three nucleotides in the middle part, and still more preferably one nucleotide exactly in the middle. Moreover, if the oligonucleotide has an even number of nucleotides, the "middle" preferably refers to four nucleotides in the middle part, and more preferably two nucleotides in the middle part.

Also, when the oligonucleotide of the present invention is used as an allele-specific probe in the Invader assay, the oligonucleotide is preferably composed of a fragment that hybridizes to the Glyma20g34340 gene and/or Glyma04g05690 gene containing a mutated site or to the complementary sequence thereof, and a fragment (flap portion) that does not hybridize to said genes or complementary sequence, which are attached to each other via the gene sequence of the mutated site or the complementary sequence thereof.

When the oligonucleotide of the present invention is to be hybridized to the nucleic acid molecules in the sample, the hybridization reaction is performed under stringent conditions.

The nucleotide sequence of the oligonucleotide of the present invention is preferably designed to have a length of at least 10 bases, more preferably 10-200 bases, still more preferably 15-150 bases, and most preferably 18-80 bases. This oligonucleotide sequence can be used as a probe for detecting the test gene and can be used as either forward (sense) primer or reverse (antisense) primer.

The oligonucleotide primer or oligonucleotide probe designed as described above can be chemically synthesized by known means/method, and it is generally synthesized using a commercially available chemical synthesizer.

The probe can be labeled with a fluorescent label (e.g., FITC, FAM, VIC, Redmond Dye, etc.) and a quencher for the fluorescent label in advance to automate the process.

5. Microarray

A microarray can be prepared by fixing one end of the oligonucleotide of the present invention described above to a support such as glass, silicon, or gel. An array of oligonucleotides is produced, for example, by photoirradiation chemical synthesis (Affymetrix), which employs a combination of solid-phase chemical synthesis with photolithographic manufacturing technique used in the semiconductor industry. By utilizing a photolithographic mask to clearly define the boundaries of the chemical reaction sites on the chip and by performing a specific chemical synthesis process, a high-density array with oligonucleotide probes attached at predetermined locations on the array can be constructed.

6. Kit

In another aspect of the invention, a kit for detecting a mutation in the Glyma20g34340 gene and/or Glyma04g05690 gene is provided, which comprises the oligonucleotide of the present invention and/or a microarray produced using said oligonucleotide. In addition to the oligonucleotide of the present invention or the microarray prepared using said oligonucleotide, such kit may also include a solution for detection reaction, an oligonucleotide as a control, a container used for the detection reaction, and an instruction manual.

Hereinafter, the present invention will be described in further detail by way of examples, although these examples are intended to illustrate the present invention and are not intended to limit the present invention.

Example 1

<Generation of Low-Furan Fatty Acid Soybean Mutant Line>

1. Plant Materials

Soybean (*Glycine max* (L.) Merr.) varieties used as the material were as follows.

(i) Fukuyutaka (ii) Toyoshirome

The soybean variety Fukuyutaka was used to generate a mutant population. M1 seeds were obtained by soaking soybean seeds (M0 seeds) in an aqueous 0.3% ethyl methane sulfonate (EMS) solution as a mutagen overnight and then rinsing them under running water for 8 hours. The M1 seeds were then sown in a field to raise M1 individuals according to a normal method. For those plants that retained fertility, one M2 seed per individual was collected and stored. The following year, the stored M2 seeds were sown again in the field to raise M2 individuals. Two thousand eight hundred thirty-one lines of M3 seeds, each individually collected from each M2 individual, were used to select mutant lines with low furan fatty acid content. Toyoshirome and Fukuyutaka were separately crossed with the mutant lines according to the procedure described below to generate segregating populations. Note that "M0" above represents the original variety prior to the mutation, "M1" is the first generation after the mutation, and subsequent generations follow as "M2", "M3", and so on.

2. Method of Analyzing Furan Fatty Acid 100-500 mg of soybean seed powder was weighed, 5 ml of hexane was added, stirred vigorously, and kept warm on an aluminum block (TAITEC: DTC-1CN) at 60° C. for 30 minutes. Next, the resultant was sonicated in an ultrasonic cleaner (SHARP: UT-204) for 30 minutes, and then filtered using a qualitative filter paper (Whatman: No. 1 ϕ82 mm) to collect the filtrate. 5 ml of hexane was again added to the residue to repeat stirring, warming at 60° C., and extraction with the ultrasonic cleaner to collect the filtrate again. Air was blown for about 30 minutes using a gas spray unit (TAITEC: EN1-25) to completely volatilize hexane contained in the filtrate. The oil/fat in the centrifuge tube was collected and used for methyl esterification of the soybean oil/fat.

4 mg of soybean oil/fat was weighed, to which 600 μl of 0.2 M KOH-MeOH was added and mixed. 80 μl of 2 M HCl was added and mixed for 1 minute, and then 600 μl of a hexane solution containing an internal standard (methyl-$d_3$ behenate, concentration 10 μg/ml) was added and mixed for 2 minutes. After centrifugation at 13,000 rpm for 3 minutes, 500 μl of the upper layer was transferred to a new 1.5 ml tube. To this tube, 500 μl of sterile water was added, mixed for 1 minute, centrifuged at 13,000 rpm for 3 minutes, and then 100 μl of the upper layer was transferred to a glass vial and used as an analysis sample in a gas chromatograph-mass spectrometer (Agilent Technologies 5977A).

1 μL of the prepared sample was injected into a gas chromatograph-mass spectrometer in splitless mode for analysis. The analysis conditions for the equipment were as follows: helium gas was used as carrier gas at a flow rate of approximately 1 ml/min, HP-88 (Agilent: φ0.25 mm×60 m) column was used, analysis time was set to 20 min, inlet temperature was set to 250° C., temperature of the mass spectrometer connection unit was set to 230° C., ion source temperature was set to 230° C., and quadrupole mass filter temperature was set to 150° C. The temperature conditions for the column oven during the analysis period were as follows: the temperature was held at 100° C. for 1 minute, then the temperature was raised to 200° C. over 5 minutes at 20° C./min, then raised to 240° C. over 4 minutes at 10° C./min, and held at 240° C. for 4 minutes. The temperature was then raised to 250° C. over 1 minute at 10° C./min and held there for 5 minutes.

The peak areas of the internal standard (IS: molecular weight 357) and furan fatty acid (F3 (3,4-dimethyl-5-pentyl-2-furannonanoic acid): molecular weight 336) were determined from the obtained chromatogram and mass spectral data, and the ratio thereof was used as phenotypic data.

3. Screening for Mutants:

From the mutant population of the 2831 lines generated with the soybean variety Fukuyutaka, 4 lines (Mutants 1-4) were identified as mutant lines associated with the production amount of furan fatty acid by analyzing the furan fatty acid in each line using the above technique. Repeated experiments using seeds derived from different individuals confirmed that the mutations in the 4 identified lines were genetically fixed (Table A, FIG. 1).

TABLE A

Furan fatty acid content in Fukuyutaka (original variety) and mutant lines (three times repeated measurements)

| Line | F3 peak area/Internal standard peak area ×1,000 | Standard deviation |
|---|---|---|
| Fukuyutaka | 33.7 | 5.39 |
| Mutant 1 | 1.0 | 0.38 |
| Mutant 2 | 4.0 | 0.37 |
| Mutant 3 | 0.8 | 0.32 |
| Mutant 4 | 3.3 | 1.04 |

4. Identification of Chromosomal Region where Mutant Gene is Located

Genetic analysis was performed to identify the mutant gene in the mutant lines selected from the soybean mutant populations. Mutant 1 and Toyoshirome were crossed through artificial selection to obtain hybrid seeds. Crossing was done in the morning on a sunny day. Toyoshirome flower from the day before flowering was used as the mother and pollen from the flower of Mutant 1 on the day of flowering was used as the father. Specifically, for the flower of Toyoshirome on the day before flowering, the calyx and petals (banner, wing, and keel) were removed with tweezers, and after visually confirming that the anthers had not split open, the anthers were removed and the stigma of the pistil was exposed. The stamen and stigma were removed with tweezers from the flower of Mutant 1 that had flowered that day, and after visually confirming that the anthers had split open, the tip of the pistil of prepared mother (Toyoshirome) was lightly touched with the tip of the stamen (pollen) to pollinate it. The resulting hybrid individual (F1 individual) was grown, and self-fertilized seeds were obtained, which were used as a segregating population (F2 population) to raise 82 individuals.

Figure 2:
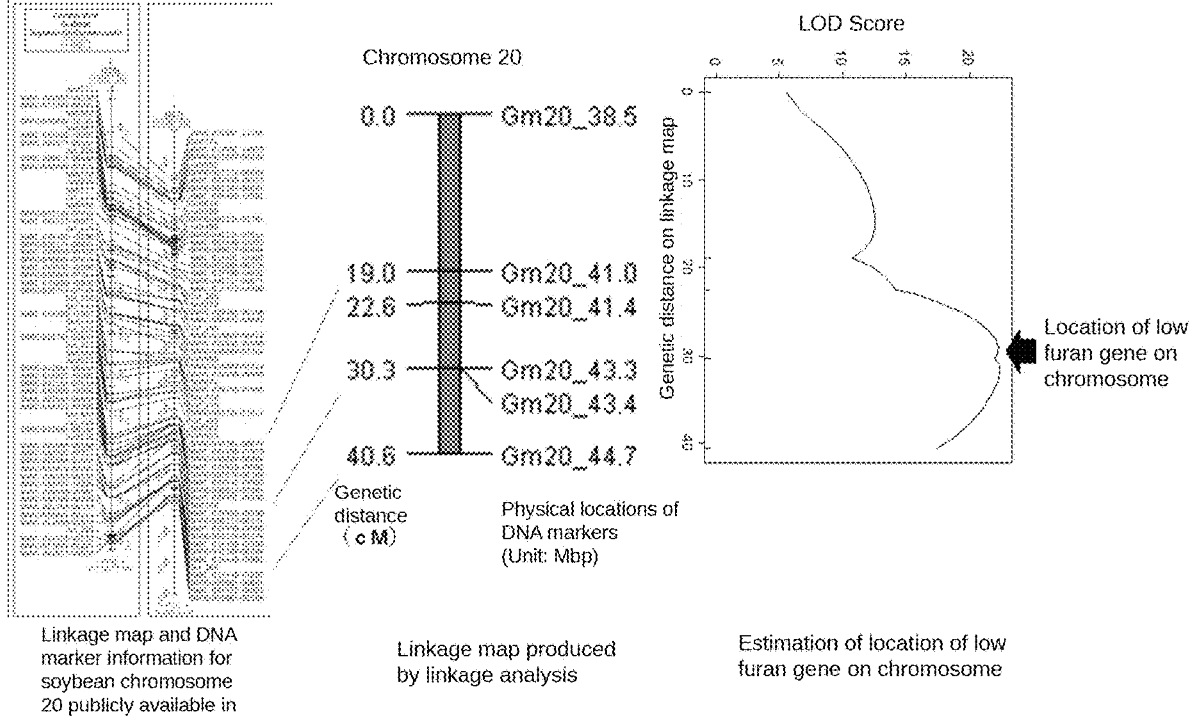
FIG. 2 Figure outlining the identification of the locus region of the mutant gene using the segregating population obtained by crossing Toyoshirome with Mutant 1.

DNA was extracted from the leaves of the 82 individuals of the segregating population obtained by crossing Toyoshirome and Mutant 1 using the method described in Yamagata, Y. et al, Breed. Sci., 2018 (hereafter, Reference A). The DNA markers indicating polymorphisms between Toyoshirome and Fukuyutaka and the genotyping technique described in Reference A were employed to determine the genotype of each individual. The self-fertilized seed of each F2 individual was also used to analyze the furan fatty acid content using the method described above. Based on the genotypic information and phenotypic data of furan fatty acid content of each individual, the chromosomal region most closely related to the genotype and phenotype of each individual was identified using the statistical analysis technique described in Md. Abdur Rauf Sarkar et al., Breed. Sci., 2020 (hereinafter, Reference B). The results of the genetic analysis showed high statistics score (LOD score) for the low furan fatty acid content characteristic of Mutant 1 in the region from 41,000,000 (41M) to 45,000,000 (45M) nucleotides of soybean chromosome 20, with the highest statistic score existing around 43.3 Mbp. Thus, we located the mutated gene responsible for the low furan fatty acid content within this region (FIG. 2). The details of References A and B mentioned above are as follows.

Reference A: Yamagata, Y., A. Yoshimura, T. Anai, and S. Watanabe, Selection criteria for SNP loci to maximize robustness of high-resolution melting analysis for plant breeding. Breed. Sci. 68: 488-498, 2018.

Reference B: Md. Abdur Rauf Sarkar, Wakana Otsu, Akihiro Suzuki, Fumio Hashimoto, Toyoaki Anai, Satoshi Watanabe, Single-base deletion in GmCHR5 increases the genistein-to-daidzein ratio in soybean seed. Breed. Sci. 70: 265-276, 2020.

5. Identification of DNA Polymorphisms Responsible for Reduced Furan Fatty Acid Content Whole genome nucleotide sequencing was performed for Mutants 1-4, Fukuyutaka, and Toyoshirome by next-generation sequencing analysis. DNA extracted from the leaves of each individual was sent to Novogene's NGS contract analysis service to acquire genomic information of 17 billion nucleotides per line. The genomic information of soybean (Gmax 189 hardmasked.fa) was acquired from public database "Phytozome" (https://phytozome.jgi.doe.gov/pz/portal.html) in the website of the "Joint Genome Institute (JGI)" (https://jgi.doe.gov/), and the nucleotide sequence information obtained from the next generation sequencing analysis of Mutants 1-4, Fukuyutaka, and Toyoshirome was compared with the genome sequence of the soybean using the method described in Reference B above to identify nucleotide polymorphisms (mutations) specific to the EMS-treated mutant lines (Mutants 1-4).

The results showed that Mutants 1-3 commonly had a nucleotide polymorphism (mutation) caused by mutagenic treatment in the Glyma20g34340 gene (gene name is indicated as Glyma.20G201400.1 or Glyma.20G201400 in version Wm82.a2.v1 of the database (Phytozome)) (Cyclopropane fatty acyl phospholipid synthase) located between 41M and 45M base pairs in soybean chromosome 20.

Specifically, Mutant 1 (also referred to as "#65") had a mutation where the 42,720,119th nucleotides in the soybean chromosome 20 sequence had been replaced from C to T (i.e., a mutation where the 1519th nucleotide, G (guanine), in the cDNA (SEQ ID NO: 1) of the Glyma20g34340 gene had been replaced by A (adenine); note that since the direction of this cDNA sequence is opposite (reverse) to that of the chromosomal sequence, the substituted nucleotide in the chromosomal sequence and the substituted nucleotide in the cDNA sequence are complementary), and the 410th amino acid in the amino acid sequence (SEQ ID NO:2) encoded by Cyclopropane fatty acyl phospholipid synthase gene had changed from glycine to aspartic acid.

Mutant 2 (also referred to as "16SN253") had a mutation where the 42,717,581st nucleotides in the soybean chromosome 20 sequence had been replaced from C to T (i.e., a mutation where the 2352nd nucleotide, G (guanine), in the cDNA (SEQ ID NO: 1) of the Glyma20g34340 gene had been replaced by A (adenine): note that since the direction of this cDNA sequence is opposite (reverse) to that of the chromosomal sequence, the substituted nucleotide in the chromosomal sequence and the substituted nucleotide in the cDNA sequence are complementary), and the 688th amino acid in the amino acid sequence (SEQ ID NO:2) encoded by Cyclopropane fatty acyl phospholipid synthase gene had changed from aspartic acid to asparagine.

Figure 3:
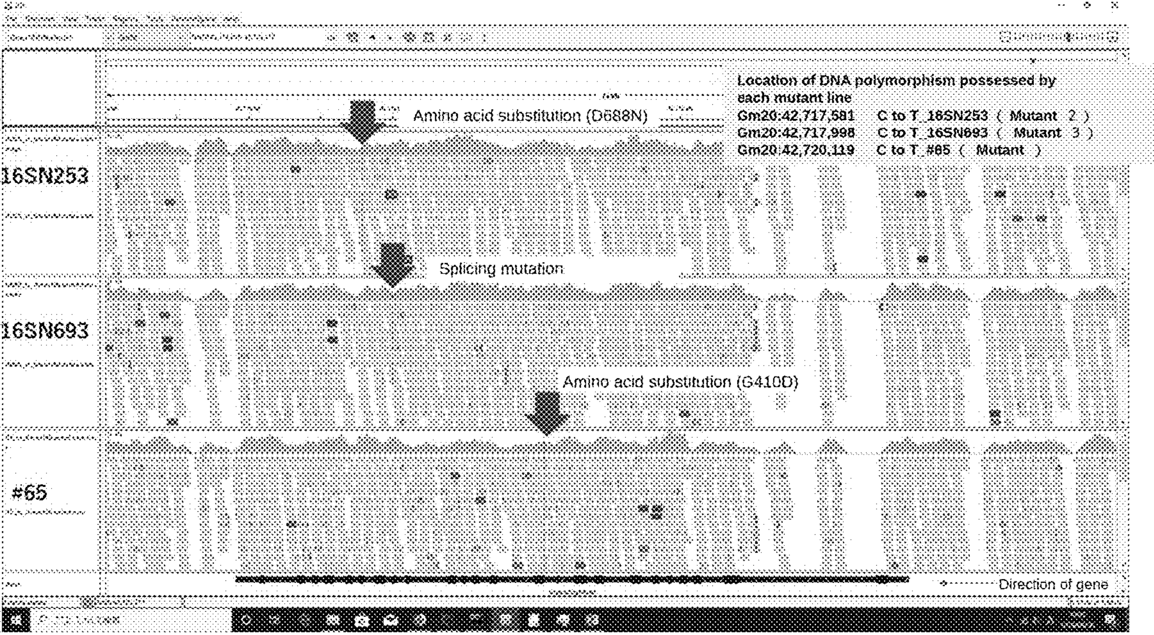
FIG. 3 Figure showing DNA polymorphisms and nucleotide polymorphisms found in the Glyma20g34340 gene for Mutants 1-3 having a phenotype of low furan fatty acid content.

Mutant 3 (also referred to as "16SN693") had a mutation where the 42,717,998th nucleotides in the soybean chromosome 20 sequence had been replaced from C to T (i.e., a mutation where the 7180th nucleotide, G (guanine), in the mRNA precursor sequence (SEQ ID NO:5) of the Glyma20g34340 gene had been replaced by A (adenine): note that since the direction of this mRNA precursor sequence is opposite (reverse) to that of the chromosomal sequence, the substituted nucleotide in the chromosomal sequence and the substituted nucleotide in the mRNA precursor sequence are complementary). As a result, sequence GU-AG, that was located on the border of the intron immediately after the 17th exon of the Cyclopropane fatty acyl phospholipid synthase gene (at both ends of said intron) and that was required for gene splicing (specifically, sequence that had "GU" at positions 7180-7181 and "AG" at positions 7267-7268 in the mRNA precursor sequence (SEQ ID NO:5) and that was required for splicing the intron (serving as a mark for splicing)) was changed to sequence AU-AG, and this was considered to cause splicing abnormality in the above intron (sequence identified by the 7180th-7268th nucleotides in SEQ ID NO:5) (FIG. 3).

For Mutant 4, since the Glyma20g34340 gene did not have the mutation caused by EMS treatment, the nucleotide sequence of the Glyma04g05690 gene listed as a homologous gene of the Glyma20g34340 gene in the database (Phytozome) (gene name is Glyma.04G054100 in version Wm82.a2.v1 of the database (Phytozome)) was used for the comparison.

Figure 4:
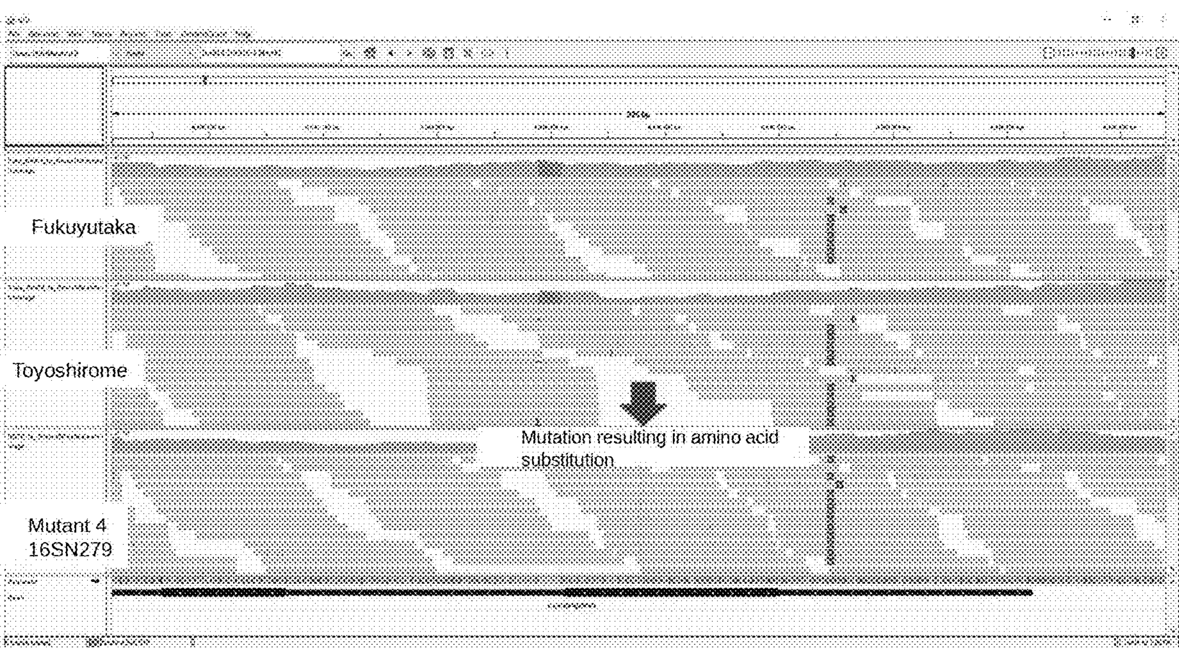
FIG. 4 Figure showing DNA polymorphism found in the Glyma04g05690 gene (Glyma04G054100 gene) for Mutant 4 having a phenotype of low furan fatty acid content.

As a result, Mutant 4 (also referred to as "16SN279") had a mutation where the 4,340,379th nucleotides in the soybean chromosome 4 sequence had been replaced from G (guanine) to A (adenine) (i.e., a mutation where the 483rd nucleotide, C (cytosine), in the cDNA (SEQ ID NO:3) of the Glyma04g05690 gene had been replaced by T (thymine); note that the substituted nucleotide in the chromosomal sequence and the substituted nucleotide in the cDNA sequence are complementary), and the 64th amino acid in the amino acid sequence (SEQ ID NO:4) encoded by the Glyma04g05690 gene had changed from arginine to cysteine (FIG. 4). The 102nd through 377th amino acids of the Glyma04g05690 gene were predicted to be involved in the function of Cyclopropane fatty-acyl-phospholipid synthase and related methyltransferases, and the 559th through 848th amino acids of Glyma20g34340 were predicted to have similar function.

Figure 5A:
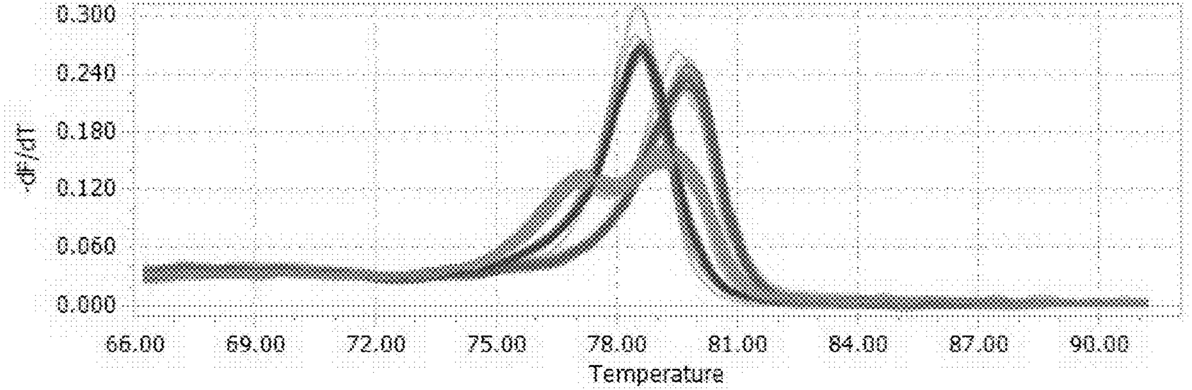
FIG. 5A Figure showing the results of genotyping for the 42,720,119th DNA polymorphisms in soybean chromosome 20 of Mutant 1 (#65) by PCR using high melting curves.
Figure 5B:
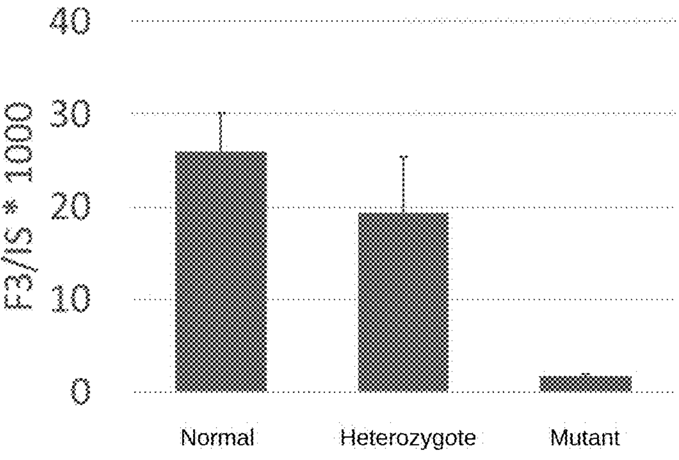
FIG. 5B Figure showing association between the 42,720,119th DNA polymorphisms in soybean chromosome 20 of Mutant 1 (#65) and the furan fatty acid contents.

6. Development of DNA Markers for DNA Polymorphisms Responsible for Reduced Furan Fatty Acid Content and their Association with Low-Furan Fatty Acid Content Phenotype DNA markers were developed for the DNA polymorphisms identified in each mutant line (Mutants 1-4) that could identify the genotype carried by each individual, and their association with the low-furan fatty acid content phenotype was confirmed. To develop DNA markers that could identify the genotypes by PCR method for DNA polymorphisms, the method described in Reference A was employed. Specifically, primers used for PCR (forward primer: ACTATACGATTGAACTTTCAGGCTT (SEQ ID NO:6), reverse primer: GCTTCCTAGAATGCCATGAGCT (SEQ ID NO:7)) were designed to sandwich the 42,720,119th nucleotides of Mutant 1 and DNA fragments containing polymorphic DNAs were amplified by PCR method using DNA of each individual as a template. The genotype of each individual was identified by detecting the difference in the nucleotides contained in the PCR fragments as the difference in the temperature at which the double-stranded DNA melts to single-stranded DNA (FIG. 5A). Since the normal type has nucleotide C and the mutant type has nucleotide T, the peak of change in the melting temperature (hereinafter referred to as melting temperature) shows a higher melting temperature for the normal type (blue plot in FIG. 5A) than for the mutant type (red plot in FIG. 5A). On the other hand, heterozygous individuals have both normal and mutant type DNAs, so the melting temperature of the PCR fragment shows a different pattern (orange plots in FIG. 5A). The furan fatty acid content exhibited by each individual in the segregating population resulting from the crossing between Toyoshirome and Mutant 1 described above could be clearly distinguished by the genotype of the DNA marker produced. Thus, the low-furan fatty acid content phenotype can be explained by the 42,720,119th nucleotide polymorphisms in Mutant 1 (FIG. 5B).

Figure 6A:
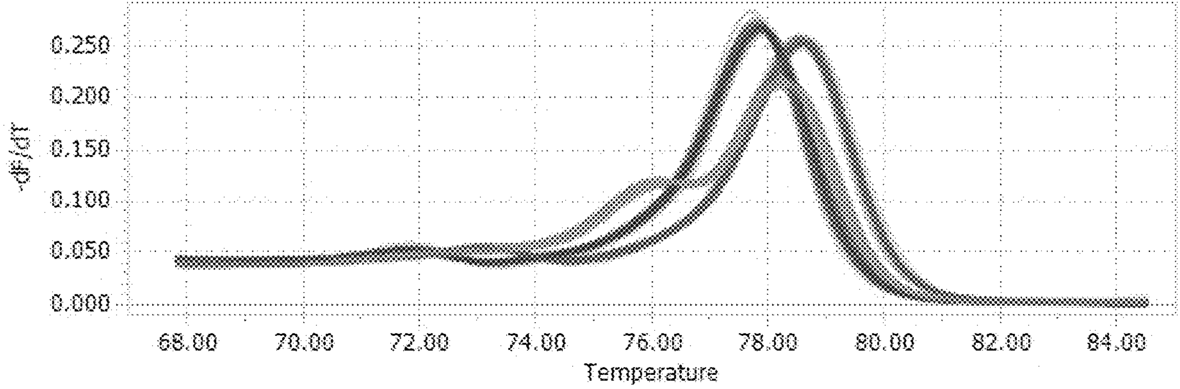
FIG. 6A Figure showing the results of genotyping for the 42,717,581st DNA polymorphisms in soybean chromosome 20 of Mutant 2 (16SN253) by PCR using high melting curves.
Figure 6B:
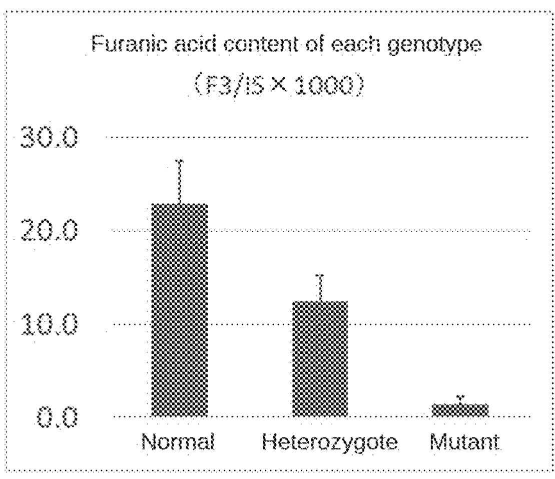
FIG. 6B Figure showing association between the 42,717,581st DNA polymorphisms in soybean chromosome 20 of Mutant 2 (16SN253) and the furan fatty acid contents.

Mutant 2 (also referred to as "16SN253") has a mutation where the 42,717,581st nucleotides of soybean chromosome 20 are replaced from C to T. Primers targeting this mutation (forward primer: TCGTATTTATATGTCTTGGGCA (SEQ ID NO:8) and reverse primer: GGACCGCATCAATTTTGT (SEQ ID NO:9)) were designed and PCR fragments containing the DNA polymorphisms of this mutant line were amplified by PCR to detect the difference in the nucleotides contained in the PCR fragments as difference in the melting temperature of the PCR fragments as described above. The normal type has nucleotide C, which shows a higher peak melting temperature than nucleotide T in the mutant type (FIG. 6A). This DNA marker was used to study the relationship between the genotypes and the furan fatty acid contents for 64 individuals from the F3 population produced by allowing the hybrid individuals obtained by crossing Fukuyutaka with Mutant 2 to undergo self-fertilization twice using the same procedure as described above. As a result, individuals with the mutant genotype expressed low-furan fatty acid content phenotype. Thus, the low-furan fatty acid content phenotype can be explained by this DNA polymorphism (FIG. 6B). The explanations for the blue, red, and orange plots in FIG. 5A also apply to those in FIG. 6A.

Figure 7A:
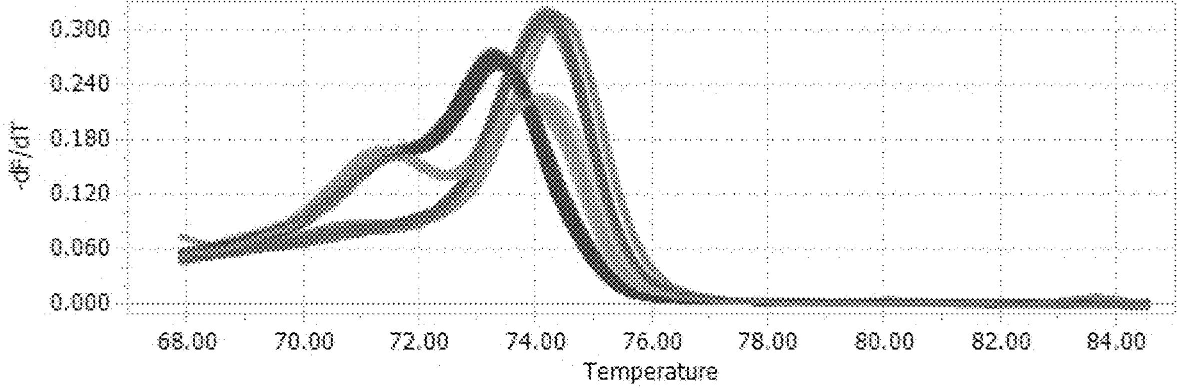
FIG. 7A Figure showing the results of genotyping for the 42,717,998th DNA polymorphisms in soybean chromosome 20 of Mutant 3 (16SN693) by PCR using high melting curves.
Figure 7B:
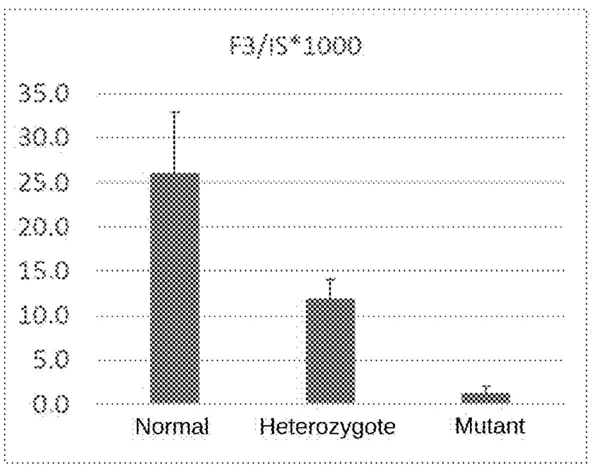
FIG. 7B Figure showing association between the 42,717,998th DNA polymorphisms in soybean chromosome 20 of Mutant 3 (16SN693) and the furan fatty acid contents.

Mutant 3 (also referred to as "16SN693") has substitution from C to T at the 42,717,998th nucleotides of soybean chromosome 20. Primers for PCR amplification targeting this mutation (forward primer: AGAAAAATCTCTCTCCTGATTGAAA (SEQ ID NO:10) and reverse primer: AGTAATAAGATAGCAATCAAAGGCA (SEQ ID NO:11)) were designed to detect the nucleotide polymorphisms contained in the PCR fragments by the difference in the melting temperature of the PCR fragments. PCR fragments having the normal allele C show a higher melting temperature than PCR fragments containing the mutant allele T (FIG. 7A). The relationship between the genotype of the DNA marker and the furan fatty acid content was studied using 32 individuals from the F2 population obtained by crossing Fukuyutaka with Mutant 3 as described above. As a result, individuals with the mutant genotype expressed low-furan fatty acid content phenotype. Thus, the low-furan fatty acid content phenotype can be explained by this nucleotide polymorphism (FIG. 7B). The explanations for the blue, red, and orange plots in FIG. 5A also apply to those in FIG. 7A.

Figure 8A:
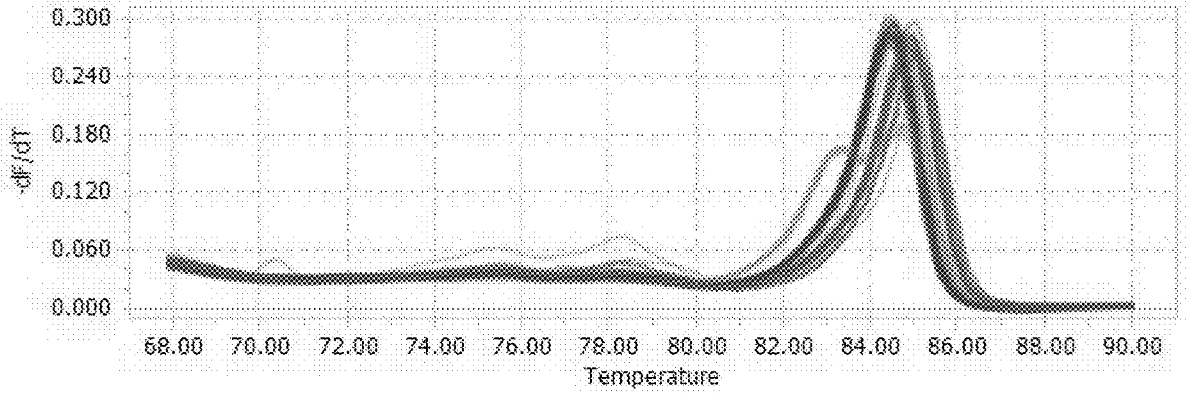
FIG. 8A Figure showing the results of genotyping for the 4,340,379th DNA polymorphisms in soybean chromosome 4 of Mutant 4 (16SN279) by PCR using high melting curves.
Figure 8B:
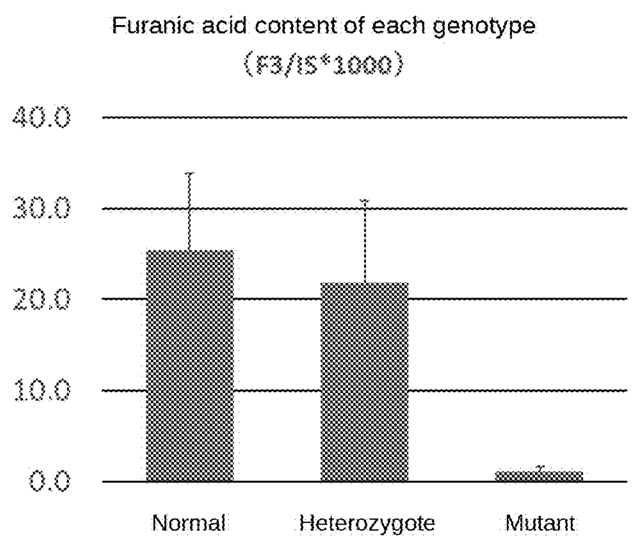
FIG. 8B Figure showing association between the 4,340,379th DNA polymorphisms in soybean chromosome 4 of Mutant 4 (16SN279) and the furan fatty acid contents.

Primers for detecting the DNA polymorphism from G to A at the 4,340,379th nucleotides in soybean chromosome 4 of Mutant 4 (also referred to as "16SN279") by PCR (forward primer: TCATCACCAGGAGACTCACG (SEQ ID NO: 12) and reverse primer: AAGTTGGGAGGAGGGTTTG (SEQ ID NO:13)) were designed to detect the nucleotide polymorphisms contained in the PCR fragments by the difference in melting temperature of the PCR fragments. If the PCR fragment has the normal nucleotide G, the melting temperature of the PCR fragment will be higher than that of the PCR fragment with the mutant nucleotide A (FIG. 8A). Using this difference in the melting temperature, the relationship between the genotypes of 63 individuals from the F3 population obtained by crossing Fukuyutaka with Mutant 4 and the furan fatty acid content was studied. As a result, individuals having the mutant gene expressed low-furan fatty acid content phenotype. Thus, the low-furan fatty acid content phenotype can be explained by this DNA polymorphism (FIG. 8B). The explanations for the blue, red, and orange plots in FIG. 5A also apply to those in FIG. 8A.

Based on the above results, Mutant lines 1~4 shown in this example were found to have a reduced furan fatty acid content in the oils/fats contained in the soybeans compared to the original variety Fukuyutaka, showing that the mutations caused in the genes that are thought to encode Cyclopropane fatty-acyl-phospholipid synthase and related methyltransferases, i.e., the Glyma20g34340 and Glyma04g05690 genes, were responsible for the reduced furan fatty acid content exhibited by each mutant line.

Example 2

<Evaluations of Oils/Fats Derived from Low-Furan Fatty Acid Soybeans and Processed Food Products Using Said Soybeans>

1. Extraction and Refinement of Soybean Oil/Fat (1) Soybean Seeds

The following seeds grown and harvested in the field at Saga University were used.

1. Fukuyutaka
2. #65 (low-furan fatty acid line): Mutant 1 produced in Example 1

(2) Extraction Conditions

Each soybean seed, which had been ground using a blender, was immersed in hexane heated to 50° C. and hexane was distilled and collected from the resulting immersion solution to extract the oil content.

(3) Refinement Conditions

The above extracted oil was refined by degumming, deacidifying, bleaching, and deodorizing, which are common refinement methods.

First, 0.4% by mass of 85% aqueous phosphoric acid solution and 2.5% by mass of warm water were added to the extracted oil heated to 80° C. After stirring for 30 minutes, the aqueous phase was centrifugally removed to obtain degummed oil.

Next, 0.05% by mass of 85% aqueous phosphoric acid solution and 0.6% by mass of 15% aqueous NaOH solution were added to the degummed oil heated to 80° C. After stirring for 15 minutes, the aqueous phase was centrifugally removed. To the resulting oil phase, 15% by mass of ion-exchanged water was added at 80° C. After stirring for 15 minutes, the aqueous phase was centrifugally removed again to obtain deacidified oil.

Next, 1.5% by mass of activated clay was added to the deacidified oil obtained above at 80° C. After stirring under reduced pressure for 30 minutes, the clay was removed by filtration to obtain bleached oil.

Next, the bleached oil obtained above was deodorized by blowing 2.0% by mass of water vapor at 250° C. under reduced pressure for 45 minutes, and 25 ppm by mass of citric acid was added to the treated oil to obtain deodorized oil.

2. Evaluation of Soybean Oils/Fats

The deodorized oil derived from each soybean seed and refined as described in section 1 above was used to evaluate the following items (1)-(3).

(1) General Properties

Fatty acid composition: Measurements were performed in accordance with Standard Methods for the Analysis of Fats, Oils and Related Materials 2.4.2.3-2013.

Furan fatty acid (F3): Measurements were performed according to the method described in paragraphs [0055]-[0058] of Japanese Patent No. 6714001 (or WO2017/033674).

(2) Light Resistance

Five grams of deodorized oil was placed in a 10 ml vial, and irradiated at 1,000 lux for one week to evaluate the following items. The furan fatty acid content of each deodorized oil was measured before light irradiation.

POV: Measurements were performed in accordance with Standard Methods for the Analysis of Fats, Oils and Related Materials 2.5.2.2-2013.

Light-induced odor: The samples irradiated with light were heated to 100° C. in a block heater and then evaluated for light-induced odor. (n=2)

(3) Heat Resistance

Hundred grams of oil was poured into a 300 mL beaker and heated at 180° C. (sampling was performed every 5 hours while heating for a total of 20 hours).

Acid value: Measurements were performed in accordance with Standard Methods for the Analysis of Fats, Oils and Related Materials 2.3.1-2013.

Color tone: Measurements were performed using a Lovibond automatic colorimeter in accordance with AOCS Cc13j-97.

Viscosity: Measurements were performed at 30° C. using an E-type viscometer.

Heat-induced odor: For the oil after 15 hours of heating, 14 panel members rated each evaluation item on a scale of 0-5 (see below), with the average value being the evaluation value.

Rating Score:
- 5: Sensed very strongly
- 4: Sensed strongly
- 3: Sensed strongly to some degree
- 2: Sensed to some degree
- 1: Did not sense much
- 0: Not sensed (4) Results The results of each of the above evaluations (1)-(3) are shown in Tables 1-7.

TABLE 1

| | Fatty acid composition (mass %) | | | | | | | | |
|---|---|---|---|---|---|---|---|---|---|
| | C16:0 | C18:0 | C18:1 | C18:2 | C18:3 | C20:0 | C22:0 | C24:0 | Other |
| Fukuyutaka | 10.1 | 3.0 | 22.8 | 55.8 | 6.8 | 0.3 | 0.4 | 0.2 | 0.6 |
| #65 | 10.6 | 3.4 | 22.8 | 55.4 | 6.1 | 0.3 | 0.4 | 0.2 | 0.9 |

TABLE 2

| Furan fatty acid (F3, ppm) | |
|---|---|
| | Furan fatty acid (F3) |
| Fukuyutaka | 116.0 |
| #65 | Below detection limit |

TABLE 3

| Results of light resistance evaluation | | |
|---|---|---|
| | POV (meq/kg) | Light-induced odor |
| Fukuyutaka | 2.1 | Light-induced odor was sensed |
| #65 | 2.3 | Light-induced odor was hardly sensed |

TABLE 4

| Results of heat resistance evaluation (color tone, 1 inch cell) | | | | | | | |
|---|---|---|---|---|---|---|---|
| | | 0 hr | 5 hr | 10 hr | 15 hr | 20 hr | 25 hr |
| Fukuyutaka | 10R + Y | 0.5 | 1.3 | 3.2 | 7 | 14.4 | 20 |
| | Rate of increase (%) | 0 | 160 | 540 | 1,300 | 2,780 | 3,900 |
| #65 | 10R + Y | 0.6 | 0.9 | 1.4 | 3.1 | 6.9 | 10 |
| | Rate of increase (%) | 0 | 50 | 133 | 417 | 1,050 | 1,567 |

TABLE 5

| Results of heat resistance evaluation (acid value) | | | | | | | |
|---|---|---|---|---|---|---|---|
| | | 0 hr | 5 hr | 10 hr | 15 hr | 20 hr | 25 hr |
| Fukuyutaka | Acid value (mg/g) | 0.05 | 0.07 | 0.10 | 0.21 | 0.39 | 0.53 |
| | Rate of increase (%) | 0 | 50 | 114 | 342 | 703 | 993 |
| #65 | Acid value (mg/g) | 0.06 | 0.06 | 0.08 | 0.11 | 0.16 | 0.23 |
| | Rate of increase (%) | 0 | 6 | 30 | 82 | 173 | 287 |

TABLE 6

| Results of heat resistance evaluation (viscosity) | | | | | | | |
|---|---|---|---|---|---|---|---|
| | | 0 hr | 5 hr | 10 hr | 15 hr | 20 hr | 25 hr |
| Fukuyutaka | Viscosity (mPa · s) | 40.96 | 44.83 | 51.08 | 65.7 | 92.8 | 120.3 |
| | Rate of increase (%) | 0 | 9 | 25 | 60 | 127 | 194 |
| #65 | Viscosity (mPa · s) | 41.94 | 44.23 | 46.67 | 52.03 | 60.22 | 68.8 |
| | Rate of increase (%) | 0 | 5 | 11 | 24 | 44 | 64 |

TABLE 7

| Results of heat resistance evaluation (heat-induced odor) | | |
|---|---|---|
| | Fukuyutaka | #65 |
| Overall Smell | 3.32 | 1.91 |
| Irritating odor | 2.45 | 1.36 |
| Rancid odor | 1.41 | 0.59 |
| Green off-odor | 0.82 | 0.50 |
| Metal-like smell | 0.32 | 0.18 |
| Paint-like smell | 0.27 | 0.09 |
| Fish-like smell | 0.45 | 0.36 |
| Sweet smell | 0.30 | 0.23 |

Furan fatty acid (F3) in the soybean oil/fat collected from #65 was below the detection limit. The soybean oil/fat collected from #65 had superior light resistance and suppressed light-induced odor compared to the soybean oil/fat collected from Fukuyutaka and else. In addition, it also had excellent heat resistance, the increases in the color tone, oxidation, and viscosity caused during heating were all suppressed, and the heat-induced odor was also suppressed.

3. Evaluation of Processed Food Products Using Soybean (1) Each soybean (Fukuyutaka, #65 (low-furan fatty acid line)) used in section 1. above was used to make prototypes of the following processed food products (i)-(v).

(i) Soybean hamburger steak
(ii) Soy milk
(iii) Bean curd
(iv) Soy pulp cookies
(iv) Soy flour cookies (2) Methods of Producing Prototypes (i) Soybean Hamburger Steak One hundred and fifty grams of each soybean was soaked in at least 4 times the amount of water overnight and boiled in a pot for 30 minutes to 1 hour.

Two hundred grams of boiled soybean was made into a paste using a food processor and kneaded well with the ingredients marked with * in Table 8.

The resultant was shaped and fried in an oiled pan.

After 3.5 minutes, the hamburger steak was turned over and fried for another 2.5 minutes to obtain a soybean hamburger steak.

TABLE 8

| Ingredients of soybean hamburger | |
|---|---|
| Ingredients | Weight |
| Boiled soybean | 200 g |
| *Egg | 25 g |
| *Breadcrumbs | 7 g |
| *Potato starch | 20 g |
| *Salt | 2.4 g |
| Commercially available deodorized soybean oil ("Rich and tasty soybean oil (Koku to umami no daizu no abura)", manufactured by J-OIL MILLS) | 14 g |

(ii) Soy Milk

One hundred and fifty grams of each soybean was soaked in water.

The soybean was lightly rinsed with water, to which 750 g of water (5 times the amount of soybean in dry state) was added, and the resultant was ground with a mixer.

The mixture was heated to boil in a pot and further heated on low heat for another 10 minutes.

The mixture was strained through a bleached cotton cloth to separate the soy pulp from the soymilk to obtain soymilk.

(iii) Bean Curd

Soy milk derived from each soybean in (ii) above was placed in a pot, heated to 75-80° C., and then the heat was turned off.

Bittern was added at 1.5% by mass to the soy milk, and the mixture was lightly stirred, covered with a lid, and steeped for 10 minutes.

Water was drained in a colander covered with a bleached cotton cloth.

(iv) Soy Pulp Cookies

The water content was squeezed out well of the soy pulp derived from each soybean that was separated from the soy milk in (ii) above, thereby obtaining raw soy pulp.

The ingredients listed in Table 9 were mixed well in a bowl.

The mixture was left to sit in the refrigerator for an hour, then shaped.

The resultant was baked in an oven preheated to 170° C. for 25 minutes to obtain soy pulp cookies.

TABLE 9

| Ingredients of soy pulp cookies | |
|---|---|
| Ingredients | Weight |
| Raw soy pulp | 60 g |
| Weak flour | 40 g |
| Sugar | 15 g |
| Egg | 40 g |
| Butter | 40 g |

(v) Soy Flour Cookies

Each soybean was ground with a mixer to obtain soy flour.

The ingredients listed in Table 10 were mixed well in a bowl.

The mixture was spread thinly and let sit in the refrigerator for an hour.

After cutting out the shapes, the resultant was baked in an oven preheated to 170° C. for 20 minutes.

TABLE 10

| Ingredients of soy flour cookies | |
|---|---|
| Ingredients | Weight |
| Soy flour | 60 g |
| Weak flour | 40 g |
| Sugar | 15 g |
| Egg | 40 g |
| Butter | 40 g |

(3) Evaluation Results

For each processed food, a panel of four people rated the "soybeaniness (beany smell)" and "astringent aftertaste (astringency)" on a scale of 1-3 (see below), with the average value being the evaluation value. The results of the evaluation are shown in Tables 11-15.

Rating Score:

1: Not sensed at all

2: Sensed to some degree

3: Clearly sensed

TABLE 11

| Flavor of soybean hamburger steak | | |
|---|---|---|
| | Fukuyutaka | #65 |
| Beany smell | 3 | 2 |
| Astringency | 3 | 1.3 |

TABLE 12

| Flavor of soy milk | | |
|---|---|---|
| | Fukuyutaka | #65 |
| Beany smell | 3 | 1.3 |
| Astringency | 2 | 1 |

TABLE 13

| Flavor of bean curd | | |
|---|---|---|
| | Fukuyutaka | #65 |
| Beany smell | 3 | 1.8 |
| Astringency | 3 | 1 |

TABLE 14

| Flavor of soy pulp cookies | | |
|---|---|---|
| | Fukuyutaka | #65 |
| Beany smell | 3 | 1 |
| Astringency | 2 | 1 |

TABLE 15

| Flavor of soy flour cookies | | |
|---|---|---|
| | Fukuyutaka | #65 |
| Beany smell | 3 | 1.3 |
| Astringency | 2.5 | 1 |

Processed food products made using #65 or a processed product of #65 soybean as an ingredient had a good flavor with both beany smell and astringency being suppressed compared to processed food products that were made using Fukuyutaka or a processed product of Fukuyutaka soybean as an ingredient.

INDUSTRIAL APPLICABILITY

The present invention can provide a modified soybean with reduced furan fatty acid content (production amount of furan fatty acid) in the oil/fat contained in the soybean. An edible oil/fat derived from this modified soybean as well as food products containing this edible oil/fat are different from those containing conventional soybean oils/fats in that the unpleasant light-induced odor peculiar to soybean oils/fats is suppressed, and that the heat-induced odor caused during heat cooking, etc., especially the irritating odor derived from soybean oils/fats, is suppressed. Furthermore, in the edible oil/fat derived from the modified soybean, the increases in viscosity, color tone and oxidation caused during heating are more suppressed than those in conventional soybean oils/fats. In addition, food products and the like containing the modified soybean or a processed product of said modified soybean have a good flavor with a suppressed beany smell. Therefore, the above modified soybean is highly useful and practical.

SEQUENCE LISTING FREE TEXT

SEQ ID NOS:6-13: Synthetic DNA

The invention claimed is:

1. A modified soybean in which a content amount of furan fatty acid in an oil/fat contained in the modified soybean has been reduced by genetic mutation, compared to an original soybean of the modified soybean, wherein the modified soybean has a mutation introduced into a gene encoding an amino acid sequence represented by SEQ ID NO: 2 or a gene encoding an amino acid sequence represented by SEQ ID NO: 4 as the genetic mutation, and the content amount of furan fatty acid in the oil/fat contained in the modified soybean is 0 ppm by mass or more and 20 ppm by mass or less.

2. The modified soybean according to claim 1, wherein the furan fatty acid is 3,4-dimethyl-5-pentyl-2-furan-nonanoic acid.

3. The modified soybean according to claim 1, wherein the mutation introduced into the gene is any of the mutations selected from the group consisting of missense mutation, nonsense mutation, frameshift mutation, and null mutation.

4. The modified soybean according to claim 1, wherein the mutation introduced into the gene encoding the amino acid sequence represented by SEQ ID NO: 2 is:

(i) a mutation of a nucleotide in the codon encoding the 410th amino acid residue of the amino acid sequence represented by SEQ ID NO: 2 encoded by the gene;

(ii) a mutation of a nucleotide in the codon encoding the 688th amino acid residue of the amino acid sequence represented by SEQ ID NO: 2 encoded by the gene; or (iii) a mutation of a nucleotide present at the boundary between the 17th exon and intron of the gene.

5. The modified soybean according to claim 4, wherein the mutation of (i) above is a mutation where a codon of glycine is replaced with a codon of aspartic acid.

6. The modified soybean according to claim 5, wherein the mutation of (i) above is a mutation where the 1519th nucleotide, G (guanine), in the cDNA of the gene encoding the amino acid sequence represented by SEQ ID NO: 2 is replaced with A (adenine).

7. The modified soybean according to claim 4, wherein the mutation of (ii) above is a mutation where a codon of aspartic acid is replaced with a codon of asparagine.

8. The modified soybean according to claim 7, wherein the mutation of (ii) above is a mutation where the 2352nd nucleotide, G (guanine), in the cDNA of the gene encoding the amino acid sequence represented by SEQ ID NO: 2 is replaced with A (adenine).

9. The modified soybean according to claim 4, wherein the mutation of (iii) above is a mutation where the 7180th nucleotide, G (guanine), in the mRNA precursor of the gene encoding the amino acid sequence represented by SEQ ID NO: 2 is replaced with A (adenine).

10. The modified soybean according to claim 1, wherein the mutation introduced into the gene encoding the amino acid sequence represented by SEQ ID NO: 4 is a mutation of a nucleotide in the codon encoding the 64th amino acid residue of the amino acid sequence represented by SEQ ID NO: 4 encoded by the gene.

11. The modified soybean according to claim 10, wherein the mutation is a mutation where a codon of arginine is replaced with a codon of cysteine.

12. The modified soybean according to claim 11, wherein the mutation is a mutation where the 483rd nucleotide, C (cytosine), in the cDNA of the gene encoding the amino acid sequence represented by SEQ ID NO: 4 is replaced with T (thymine).

13. The modified soybean according to claim 1, which is modified Fukuyutaka soybean.

14. LF65 soybean whose accession number is FERM BP-22392.

15. 16SN279 soybean whose accession number is FERM BP-22413.

16. An ingredient for food products, feed products or pharmaceutical compositions, the ingredient comprising the modified soybean according to claim 1 or a processed product thereof.

17. A food product, feed product or pharmaceutical composition comprising the ingredient according to claim 16.

18. A method for producing a modified soybean, the method comprising crossing the modified soybeans according to claim 1 with each other, or crossing said modified soybean with other soybean species.

* * * * *